(12) United States Patent
Ghoshal et al.

(10) Patent No.: US 7,569,676 B2
(45) Date of Patent: Aug. 4, 2009

(54) ECSTASY-CLASS DERIVATIVES, IMMUNOGENS, AND ANTIBODIES AND THEIR USE IN DETECTING ECSTASY-CLASS DRUGS

(75) Inventors: Mitali Ghoshal, Noblesville, IN (US); Gerald F. Sigler, Carmel, IN (US); Richard Terry Root, Fishers, IN (US); Anlonga Ouyang, Indianapolis, IN (US); Salvatore J. Salamone, Stockton, NJ (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 267 days.

(21) Appl. No.: 11/076,569

(22) Filed: Mar. 9, 2005

(65) Prior Publication Data

US 2005/0153439 A1  Jul. 14, 2005

Related U.S. Application Data

(62) Division of application No. 10/622,254, filed on Jul. 18, 2003, now Pat. No. 7,060,847.

(51) Int. Cl.
*C07K 16/00* (2006.01)
*C12N 5/12* (2006.01)
*C12N 5/18* (2006.01)

(52) U.S. Cl. ............... 530/388.9; 435/70.2; 435/70.21; 435/345; 530/809

(58) Field of Classification Search ............ 530/388.9, 530/389.8, 809; 435/345, 70.2
See application file for complete search history.

(56) References Cited

U.S. PATENT DOCUMENTS

| 4,041,076 A | 8/1977 | Avenia et al. |
| 5,470,997 A | 11/1995 | Buechler et al. |
| 5,501,987 A | 3/1996 | Ordonez et al. |
| 5,618,926 A | 4/1997 | Salamone et al. |
| 5,976,812 A | 11/1999 | Huber et al. |
| 6,946,547 B2 * | 9/2005 | Rouhani et al. ......... 530/388.9 |
| 2003/0175995 A1 * | 9/2003 | Hui ......................... 436/547 |
| 2004/0121400 A1 * | 6/2004 | McConnell et al. ........ 435/7.1 |

FOREIGN PATENT DOCUMENTS

| EP | 0329326 | 8/1989 |
| EP | 1167976 A2 * | 1/2002 |
| GB | 2361473 | 3/2000 |

OTHER PUBLICATIONS

Cody, J.T. et al., "Flourescence Polarization Immunoassay Detection of Amphetamine, Methamphetamine, and Illicit Amphetamine Analogues," Journal of Analytical Toxicology, vol. 17, Jan./Feb. 1993. pp. 26-30.

Hadri, A. et al., "Synthesis and bovine Beta3-adrenergic agonistic activities of a novel series of aryloxypropanolamines," Pharmazie, vol. 56, No. 7, 2001, pp. 517-522.

Kunsman, G.W. et al., "Application of the Syva EMIT and Abbott TDx Amphetamine Immunoassays to the Detection of 3,4-Methylenedioxymethamphetamine (MDMA) and 3,4-Methylenedioxyethamphetamine (MDEA) in Urine," Journal of Analytical Toxicology, vol. 14, May/Jun. 1990. pp. 149-153.

Poklis, A. et al., Emit-d.a.u. Monoclonal Amphetamine/Methamphetamine Assay. II. Detection of Methylenedioxyamphetamine (MDA and Methylenedioxymethamphetamine (MDMA)' Forensic Science International, 59 (1993) 63-70.

Zhao, H. et al., "Profiles of Urine Samples Taken from Ecstasy Users at Rave Parties: Analysis by Immunoassays, HPLC, and GC-MS," Journal of Analytical Toxicology, vol. 25, May/Jun. 2001, pp. 258-269.

* cited by examiner

*Primary Examiner*—Mary (Molly) E. Ceperley
*Assistant Examiner*—Shafiqul Haq
(74) *Attorney, Agent, or Firm*—Marilyn Amick; Roche Diagnostics Operations, Inc.

(57) ABSTRACT

The present invention comprises novel analogs of ecstasy-class compounds and novel ecstasy-class immunogens leashed out of, i.e., derived from, the methylenedioxy position. The invention also comprises unique monoclonal antibodies generated using MDO-leashed MDMA immunogens as well as unique conjugates and tracers. These antibodies, conjugates, and tracers are useful in immunoassays for the detection of ecstasy-class compounds in biological fluids.

6 Claims, 13 Drawing Sheets

ECSTASY-CLASS DERIVATIVES, IMMUNOGENS, AND ANTIBODIES AND THEIR USE IN DETECTING ECSTASY-CLASS DRUGS

RELATED APPLICATIONS

This application is a divisional of U.S. Ser. No. 10/622,254 filed Jul. 18, 2003 now U.S. Pat. No. 7,060,847.

FIELD OF THE INVENTION

This invention relates generally to the field of methods for determination of drugs of abuse in biological samples, and more particularly, to immunoassay methods for the detection of 3,4-methylenedioxymethamphetamine (MDMA) and derivatives and metabolites of MDMA, i.e., ecstasy-class compounds.

BACKGROUND OF THE INVENTION

The amphetamine analogs of methylenedioxyphenylalkylamines are a series of compounds often referred to as designer amphetamines. These psychotropic drugs are ring-substituted derivatives chemically related to mescaline. They include 3,4-methylenedioxyamphetamine (MDA), 3,4-methylenedioxymethamphetamine (MDMA, Ecstasy), 3,4-methylenedioxyethamphetamine (MDE, Eve), 3,4-methylenedioxyethylamphetamine (MDEA), 3,4-methylenedioxy-N-propylamphetamine (MDPA), 3,4-methylenedioxy-N-methylbutanamine (MBDB), and 3,4-methylenedioxybutanamine (BDB), the most common of these being MDMA.

The abuse of these designer amphetamines is increasing throughout the world, and their detection by screening methods is becoming a more important issue. Zhao, H. et al., *J. Anal. Toxicology*, Vol. 25, pp. 258-269 (2001) found 71% of urine samples from rave party attendees contained MDMA or MDA alone or in combination with amphetamine or other designer amphetamines such as MDEA.

Gas chromatography/mass spectrometry (GC/MS) is highly specific and has been described for the simultaneous detection of MDMA, MDA, amphetamine, methamphetamine, MDEA and their metabolites. GC/MS analysis is usually required for confirmation and verification of the results of an immunological assay or a suspected diagnosis. In this technique, MDMA or designer drugs are extracted in solid phase, then derivatized and analyzed via GC/MS. However, some medical facilities may not be able to detect ecstasy-class drugs because they lack the sophisticated and expensive instrumentation required.

In testing for drugs of abuse, immunoassays, particularly competitive binding immunoassays, have proven to be especially advantageous. In competitive binding immunoassays, an analyte in a biological sample competes with a labeled reagent, or analyte analog, or tracer, for a limited number of receptor binding sites on antibodies specific for the analyte and analyte analog. Enzymes such as β-galactosidase and peroxidase, fluorescent molecules such as fluorescein compounds, radioactive compounds such as $^{125}$I, and microparticles are common labeling substances used as tracers. The concentration of analyte in the sample determines the amount of analyte analog which will bind to the antibody. The amount of analyte analog that will bind is inversely proportional to the concentration of analyte in the sample, because the analyte and the analyte analog each bind to the antibody in proportion to their respective concentrations. The amount of free or bound analyte analog can then be determined by methods appropriate to the particular label being used.

Until recently, there were no commercial immunoassays designed specifically for the detection of ecstasy-class drugs, and their detection therefore depended upon the relative cross-reactivities they exhibit in the amphetamine or methamphetamine screening method used. In general, the cross-reactivity of the commercially available amphetamine and methamphetamine assays toward many of these compounds is low, which means that the assays fail to detect ecstasy-class compounds at lower concentrations, which suggests the possibility that some positive samples may go undetected. Moreover, existing immunoassays for amphetamine and methamphetamine are limited by their cross-reactivity to allergy and cold medications such as ephedrine, pseudoephedrine and phenylpropanolamine, and to diet drugs such as phentermine. This cross-reactivity factor prevents the cut-off level for detection of amphetamine and methamphetamine from being lowered, which in turn, prevents detecting ecstasy-class drugs at lower concentrations. Therefore, an assay with increased specificity for ecstasy-class compounds is needed, either as an assay to detect ecstasy-class compounds alone or as an assay to detect ecstasy-class compounds as well as amphetamine and methamphetamine.

Amphetamine and methamphetamine antibodies with significant cross-reactivity to one or more members of the ecstasy class of drugs are well known (Cody, J., *J. Anal. Toxicology* 14:321, 1990).

The synthesis of substituted methylenedioxy (MDO) leashed aromatic compounds are known in the literature (European Patent Application 329,326, published Aug. 23, 1989).

UK Patent Application 2,361,473, published Oct. 24, 2001, describes ecstasy-class analogs for detection of ecstasy-class compounds in biological samples. The conjugates and immunogens described are derived out of the nitrogen position of MDA. The present application describes an alternate solution to the problem, i.e., conjugates and immunogens derived out of the carbon position of the MDO moiety of ecstasy-class compounds.

SUMMARY OF THE INVENTION

The present invention comprises novel analogs of ecstasy-class compounds and novel ecstasy-class immunogens leashed out of, i.e., derived out of the carbon position of the MDO moiety of ecstasy-class compounds. The invention also comprises unique monoclonal antibodies generated using MDO-leashed MDMA immunogens as well as unique conjugates and tracers. These antibodies, conjugates, and tracers are useful in immunoassays for the detection of ecstasy-class compounds in biological fluids.

The present invention describes novel derivatives of ecstasy-class compounds having a linking group at the methylenedioxy position:

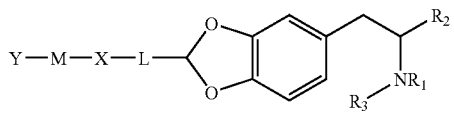

where L is CO or $CH_2$, X is NH or O, M is a saturated or unsaturated, aliphatic or aromatic, substituted or unsubstituted, straight or branched chain of 0-10 carbon or hetero atoms, Y is an activated functionality selected from the group consisting of active esters, isocyanates, isothiocyanates, thiols, imidoesters, anhydrides, maleimides, thiolactones, diazonium groups, and aldehydes, $R_1$ is H, $CH_3$, $C_2H_5$, or $C_3H_7$, $R_2$ is $CH_3$ or $C_2H_5$, and $R_3$ is a protecting group or H.

The present invention also describes novel conjugates having a linking group at the carbon position of the MDO moiety of ecstasy-class compounds:

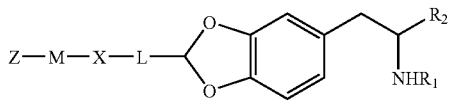

where $R_1$ is H, $CH_3$, $C_2H_5$, or $C_3H_7$, $R_2$ is $CH_3$ or $C_2H_5$, Z is a carrier molecule, L is CO or $CH_2$, X is NH or O, M is a saturated or unsaturated, aliphatic or aromatic, substituted or unsubstituted, straight or branched chain of 0-10 carbon or hetero atoms.

DETAILED DESCRIPTION OF THE INVENTION

Figure 1:
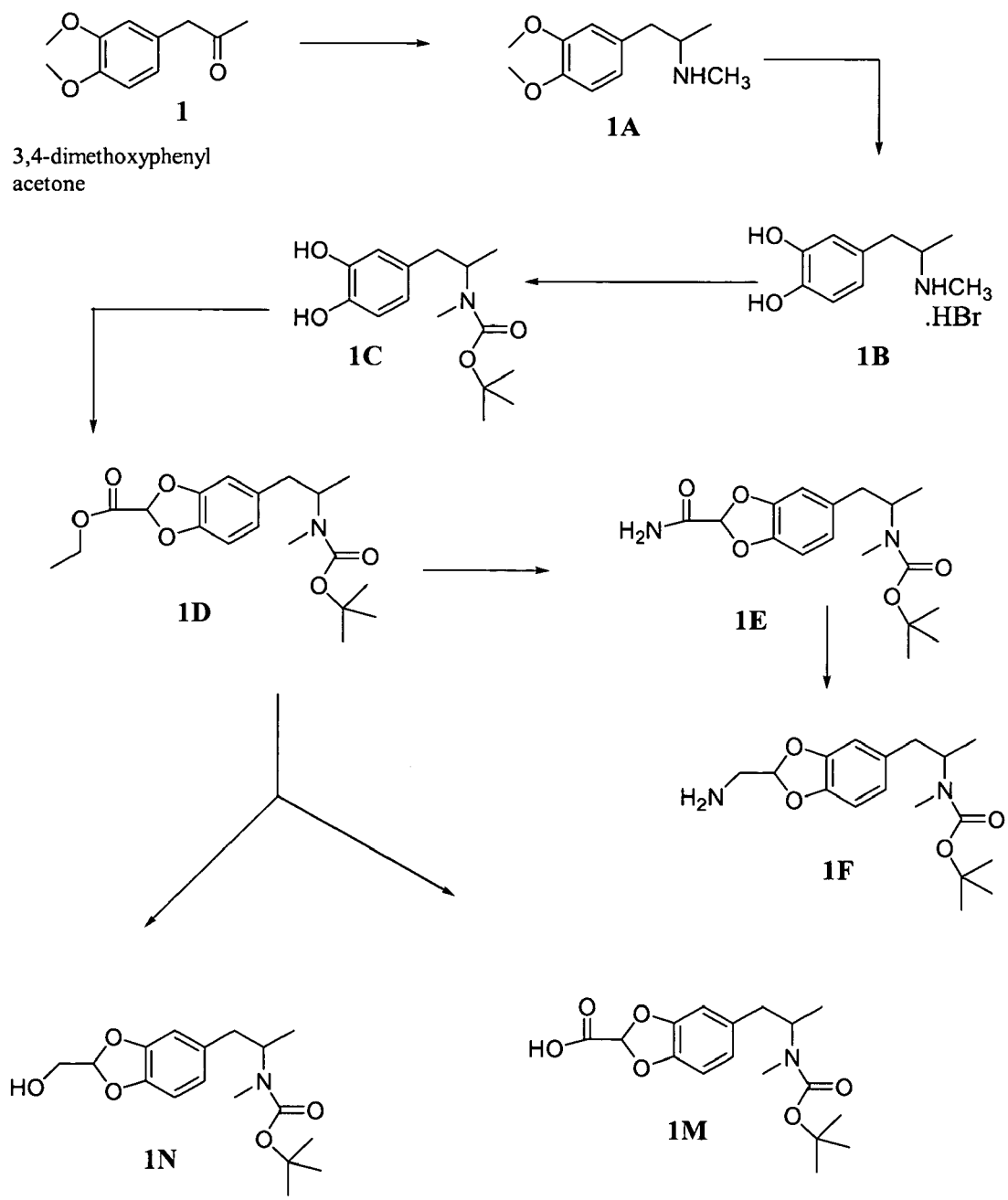
FIG. 1 is a schematic representation of a synthetic method for amino (1F), hydroxyl (1N) and carboxyl functionalized (1M) t-BOC protected MDMA derivatives.
Figure 2:
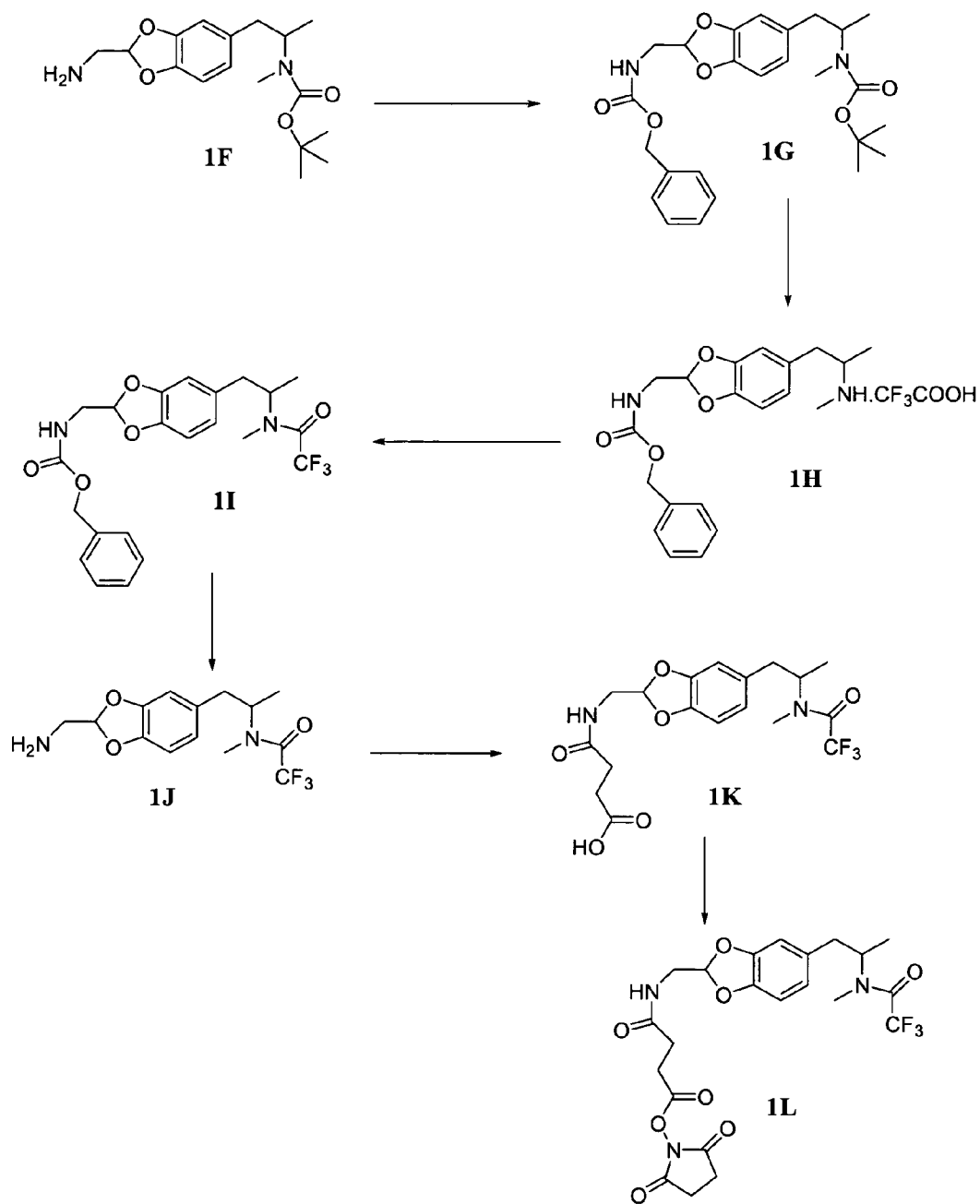
FIG. 2 is a schematic representation of a synthetic method for an N-hydroxysuccinimide ester of a trifluoroacetamido protected MDMA activated hapten derivative (1L).
Figure 3:
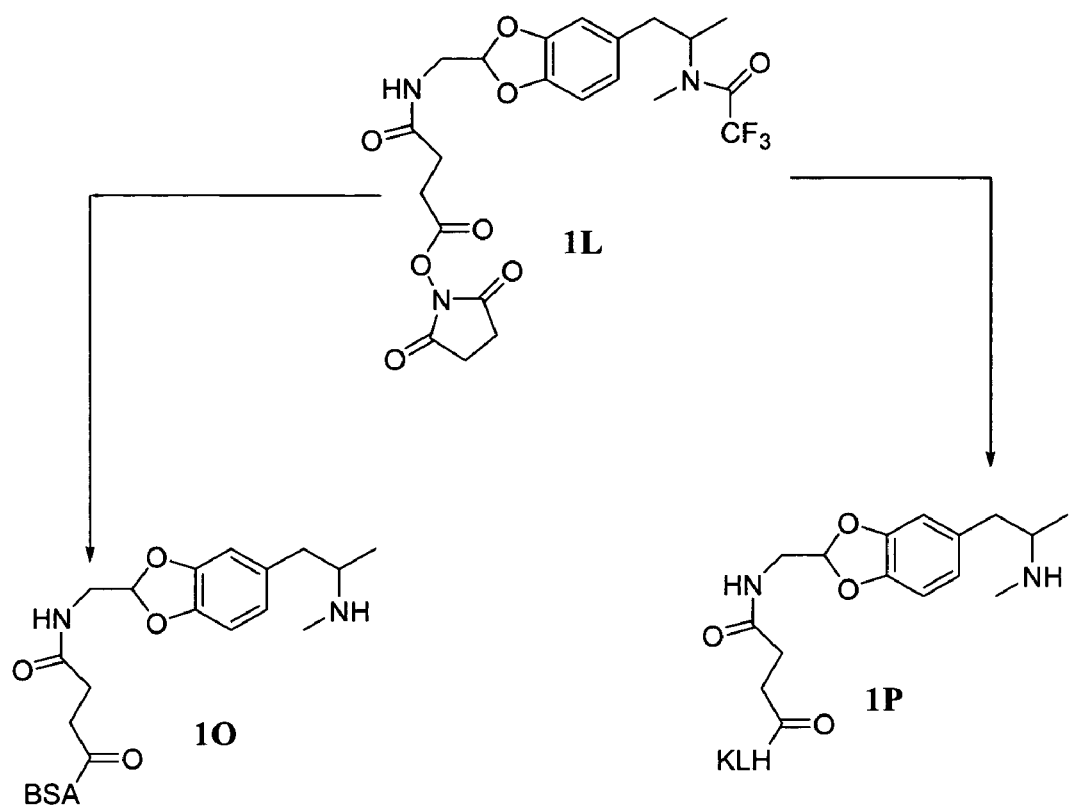
FIG. 3 is a schematic representation for the synthesis of MDMA immunogen (1P) and MDMA-BSA conjugate (1O) from MDMA activated hapten derivative (1L).
Figure 4:
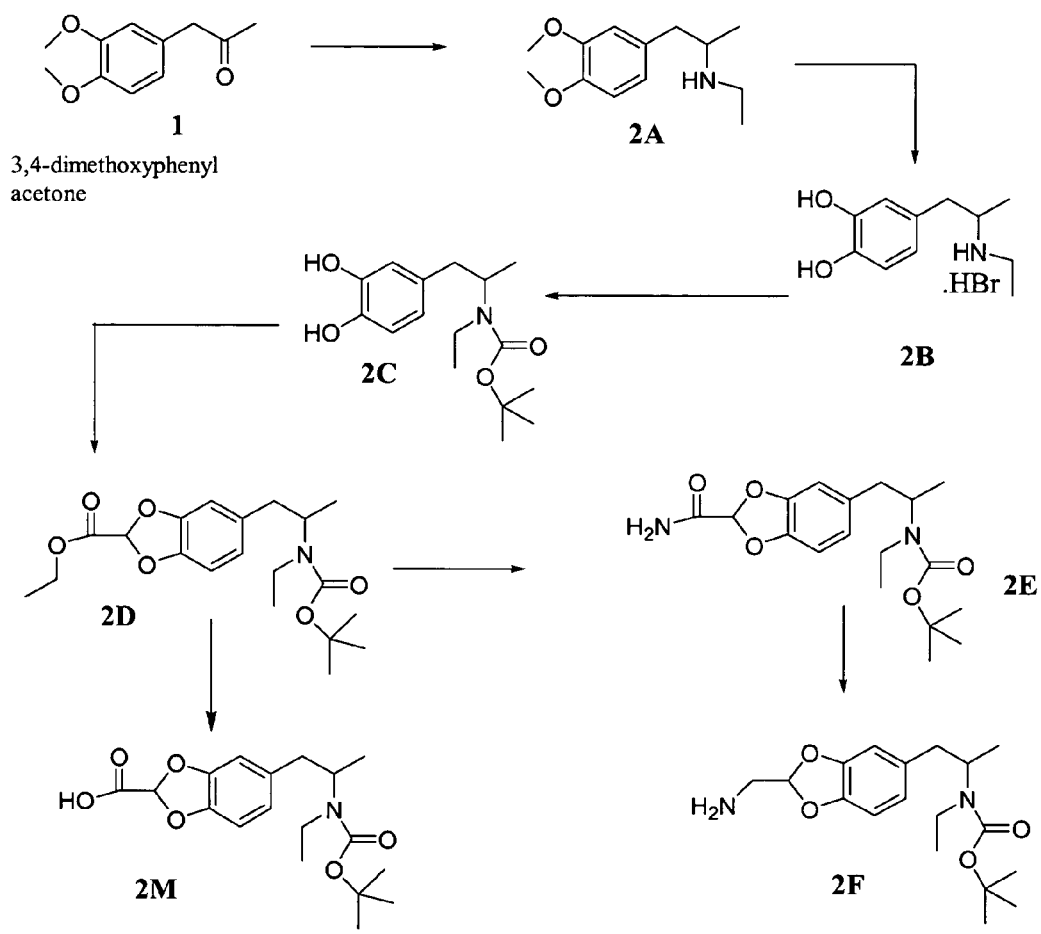
FIG. 4 is a schematic representation of a synthetic method for amino (2F) and carboxyl functionalized (2M) t-BOC protected MDEA derivatives.
Figure 5:
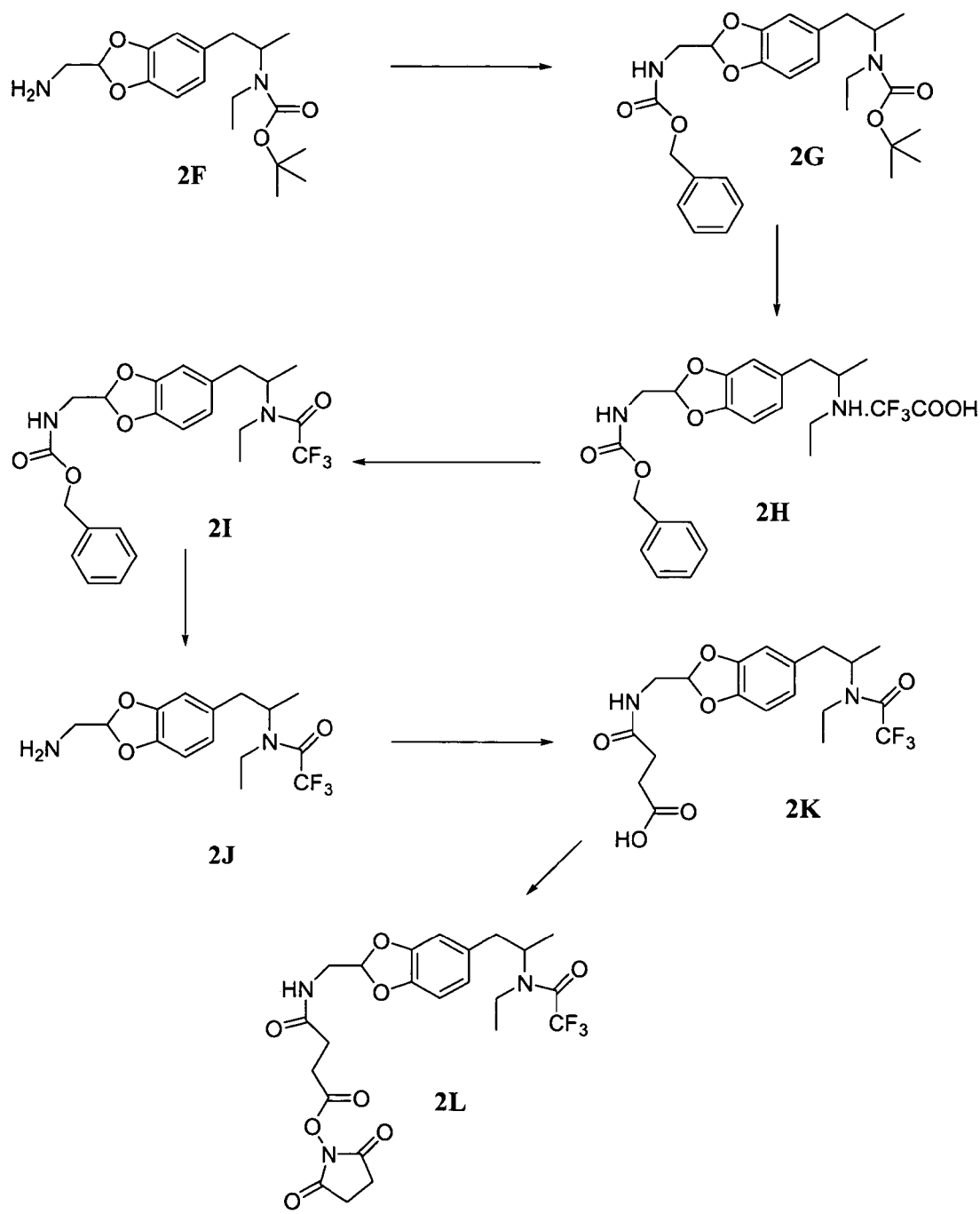
FIG. 5 is a schematic representation of a synthetic method for an N-hydroxysuccinimide ester of a trifluoroacetamido protected MDEA activated hapten derivative (2L).
Figure 6:
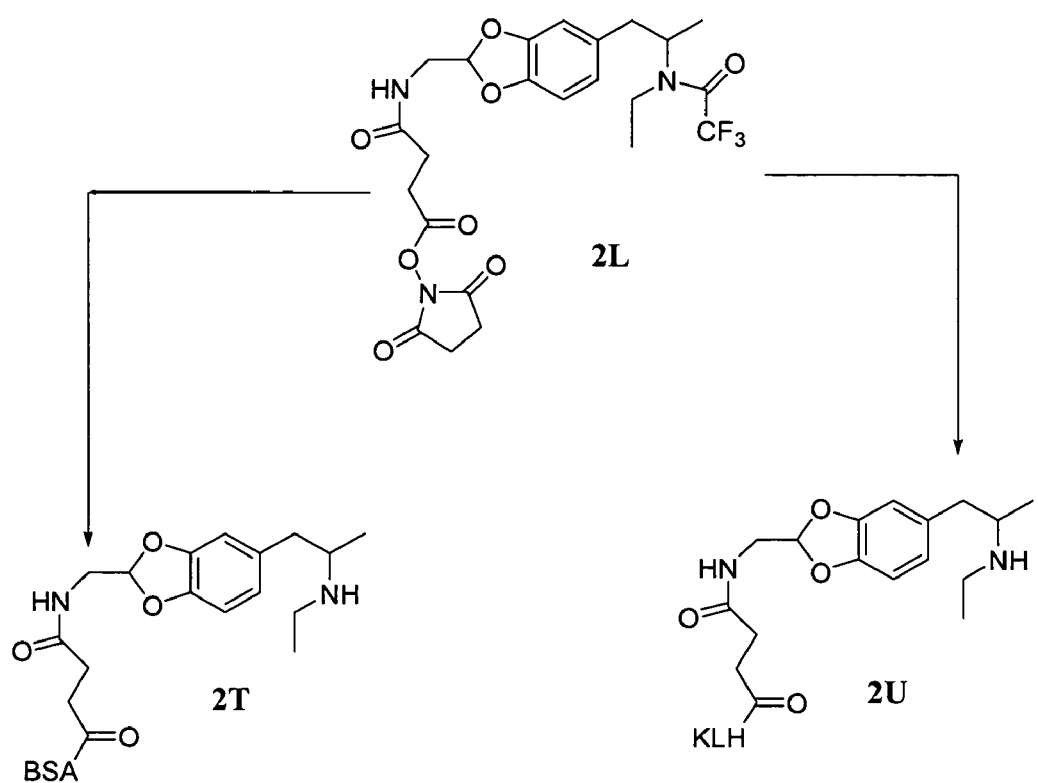
FIG. 6 is a schematic representation for the synthesis of the MDEA immunogen (2U) and MDMA-BSA screening conjugate (2T) from MDEA activated hapten derivative (2L).
Figure 7:
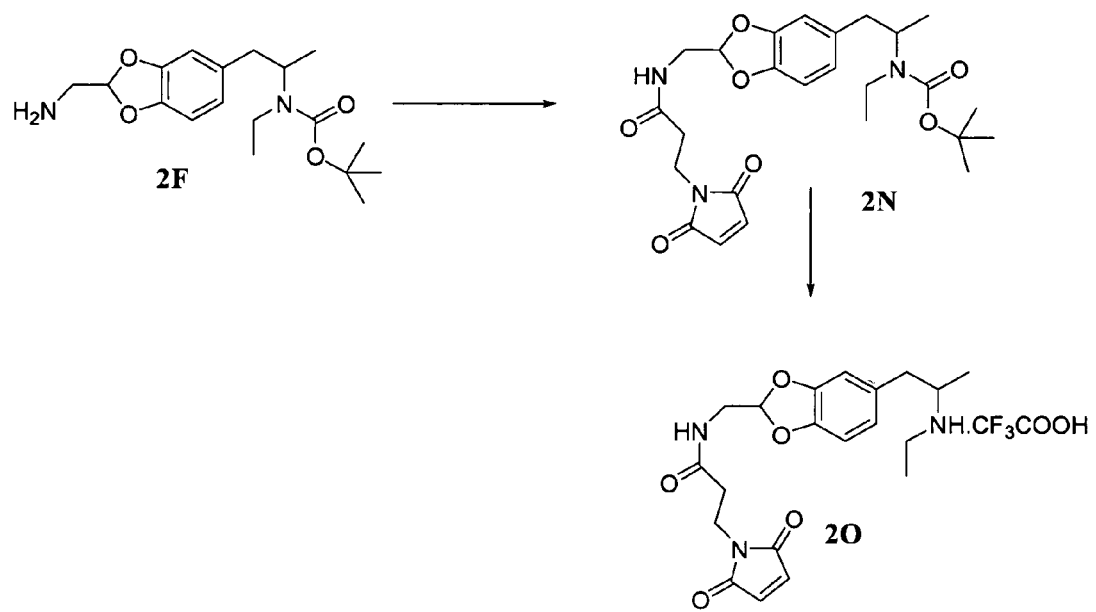
FIG. 7 is a schematic representation for the synthesis of MDEA maleimido derivative (2O) from amino derivative (2F).
Figure 8:
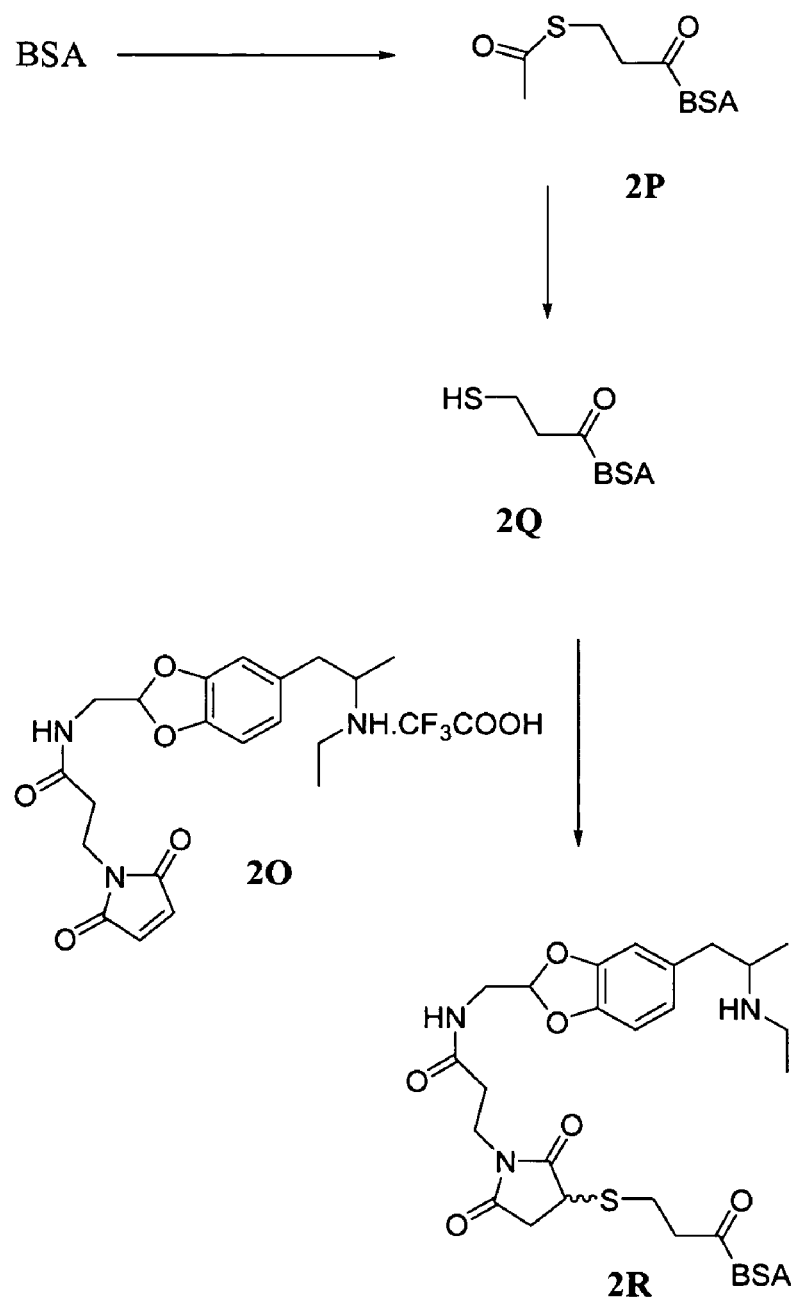
FIG. 8 is a schematic representation for the synthesis of the MDEA-maleimido-BSA conjugate (2R) from MDEA maleimido derivative (2O) and thiolated BSA.
Figure 9:
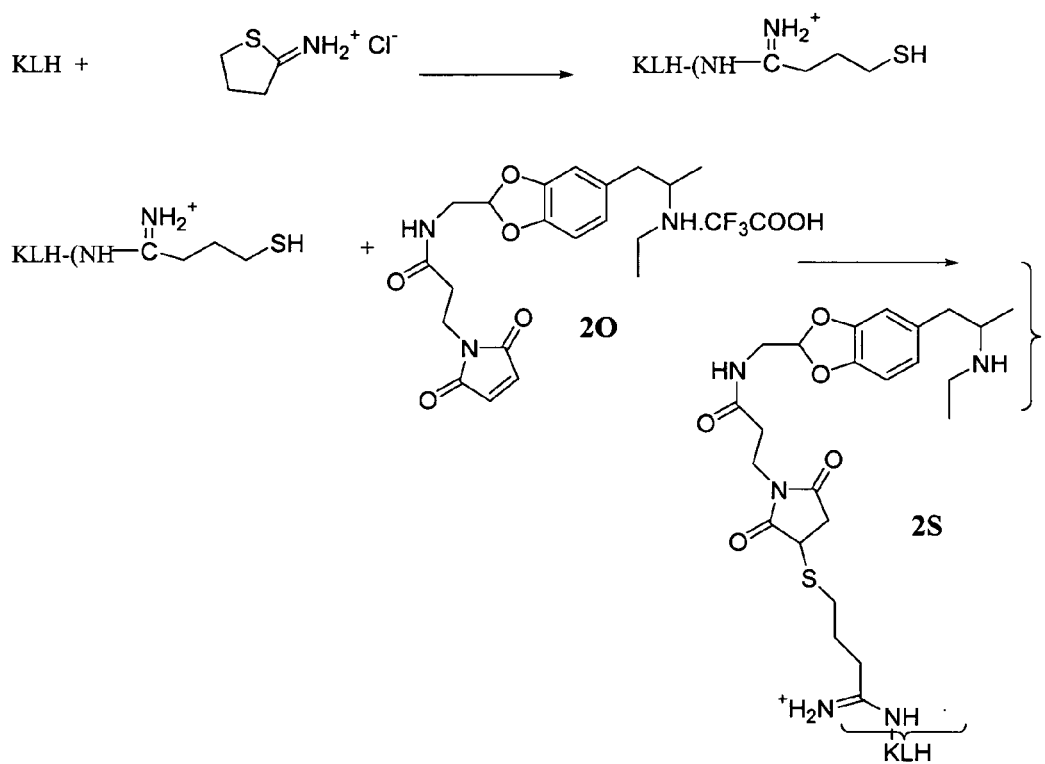
FIG. 9 is a schematic representation for the synthesis of MDEA-maleimido-KLH conjugate (2S) from MDEA maleimido derivative (2O) and thiolated KLH.
Figure 10:
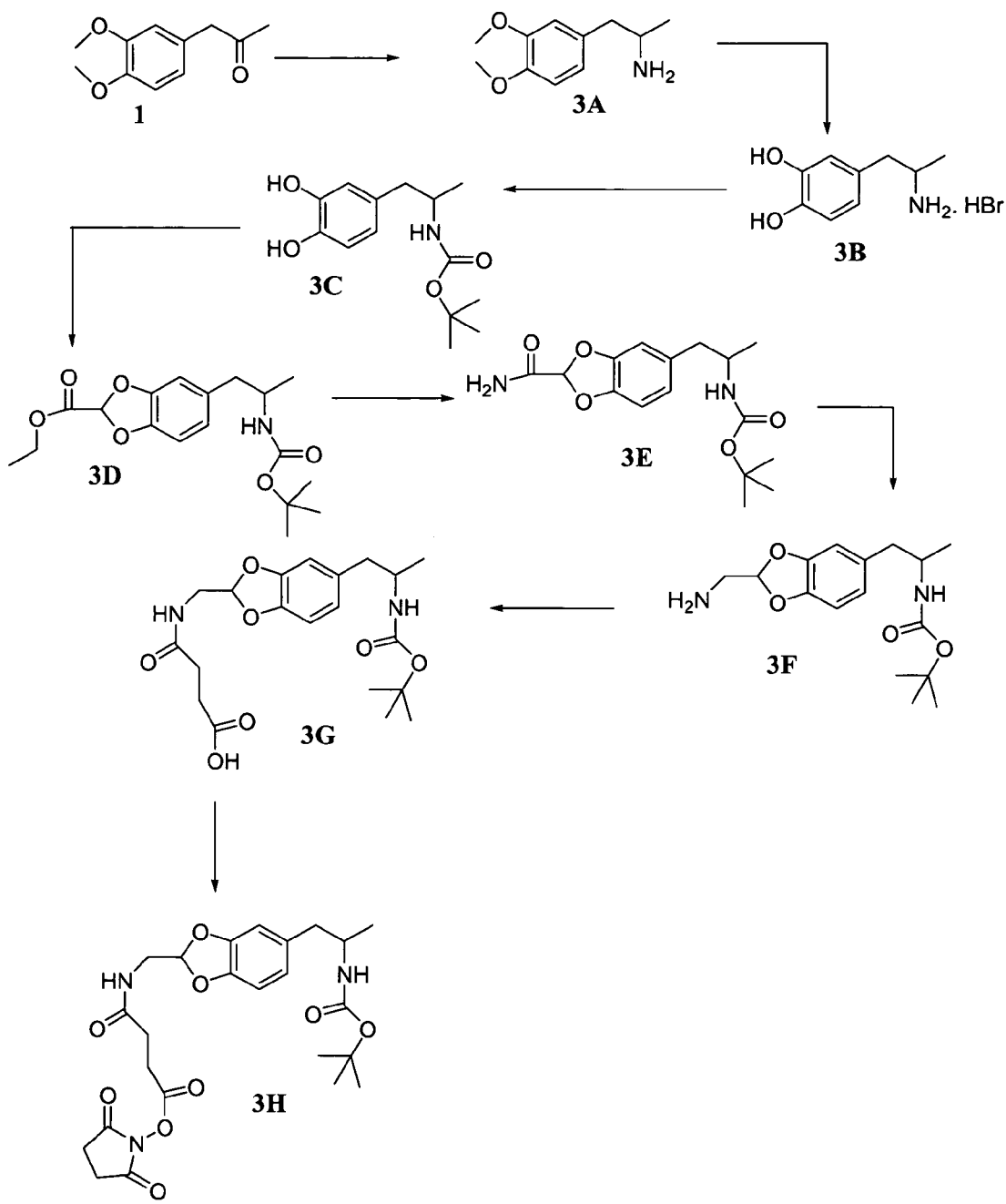
FIG. 10 is a schematic representation for the synthesis of MDA activated hapten (3H).
Figure 11:
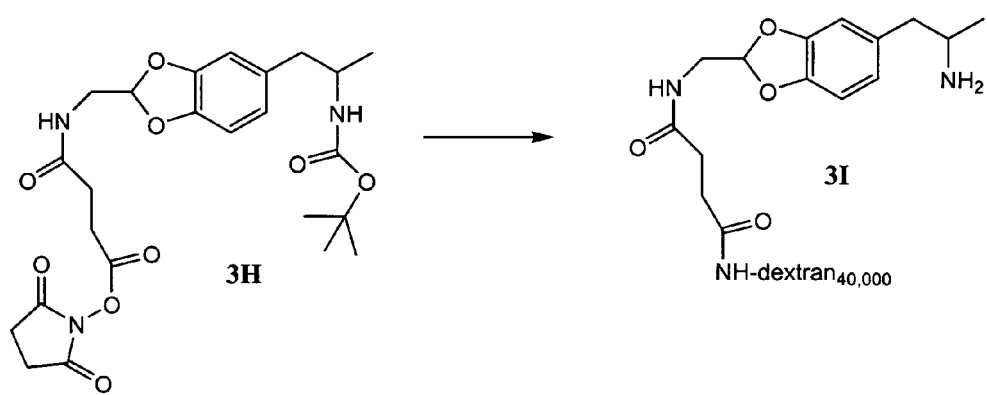
FIG. 11 is a schematic representation for the synthesis of MDA aminodextran conjugate (3I).

Compounds, e.g., haptens, intermediates, and immunogens useful in the production of antibodies specific for ecstasy-class compounds, antibodies specific for ecstasy-class compounds, reagent kits containing antibodies specific for ecstasy-class compounds, methods of producing antibodies specific for ecstasy-class compounds, and methods of detecting analytes including members of the ecstasy-class of compounds have been discovered and are described herein.

Throughout this description and in the appended claims, the following definitions are to be understood.

By "methylenedioxy amphetamines," "MD class compounds," or "ecstasy-class compounds," is meant the group of amphetamine analogs of methylenedioxyphenylalkylamines having a fused methylenedioxy-phenyl ring system including 3,4-methylenedioxyamphetamine (MDA), 3,4-methylenedioxymethamphetamine (MDMA, Ecstasy), 3,4-methylenedioxyethamphetamine (MDEA, Eve), 3,4-methylenedioxy-N-propylamphetamine (MDPA), 3,4-methylenedioxy-N-methylbutanamine (MBDB), and 3,4-methylenedioxybutanamine (BDB). As drug designers continue to synthesize new compounds which fall within the ecstasy class, this class continues to grow. Accordingly, as used herein, ecstasy class compounds includes compounds already synthesized or identified as well as those which have yet to be synthesized or identified.

The terms "immunogen" and "immunogenic" refer to substances capable of eliciting, producing, or generating an immune response in an organism.

The term "conjugate" refers to any substance formed from the joining together of two parts. Representative conjugates in accordance with the present invention include those formed by the joining together of a small molecule and a large molecule, such as a protein. The term conjugate subsumes the term immunogen.

"Haptens" are partial or incomplete antigens. They are protein-free substances, mostly low molecular weight substances, which are not capable of stimulating antibody formation, but which do react with antibodies. The latter are formed by coupling a hapten to a high molecular weight carrier and then injecting this coupled product, i.e., immunogen, into a human or animal subject. MDA, MDMA, MDEA, MBDB, BDB, and MDPA are haptens.

The term "activated hapten" refers to a hapten that has been provided with an available reaction site, for example, by the attachment of a linking group carrying a reactive moiety, that can be used to connect the hapten to a carrier, immunogen, label, tracer or other moiety.

As used herein, a "linking group" or "linker" refers to a portion of a chemical structure which connects two or more substructures such as haptens, carriers, immunogens, labels, tracers or other linkers. A linking group has at least 1 uninterrupted chain of atoms other than hydrogen (or other monovalent atoms) extending between the substructures. The atoms of a linking group and the atoms of a chain within a linking group are themselves connected by chemical bonds. Linkers may be straight or branched, saturated or unsaturated, carbon chains. They may also include one or more heteroatoms within the chain or at termini of the chains. By "heteroatoms" is meant atoms other than carbon which are chosen from the group consisting of oxygen, nitrogen and sulfur. Linking groups may also include cyclic or aromatic groups as part of the chain or as a substitution on one of the atoms in the chain.

The number of atoms in a linking group or linker is determined by counting the atoms other than hydrogen. The number of atoms in a chain within a linking group is determined by counting the number of atoms other than hydrogen along the shortest route between the substructures being connected. Linking groups may be used to activate, e.g., provide an available site on a hapten for synthesizing a conjugate of a hapten with a label or carrier.

A "carrier" or "immunogenic carrier," as the terms are used herein, is an immunogenic substance, commonly a protein, that can join with a hapten, thereby enabling the hapten to induce an immune response and elicit the production of antibodies that can bind specifically with the antigen (hapten). Carrier substances include proteins, glycoproteins, complex polysaccharides, particles, and nucleic acids that are recognized as foreign and thereby elicit an immunologic response from the host.

Various protein types may be employed as a poly(amino acid) immunogenic carrier. These types include albumins, serum proteins, e.g., globulins, ocular lens proteins, lipoproteins, etc. Illustrative proteins include bovine serum albumin (BSA), keyhole limpet hemocyanin (KLH), egg ovalbumin, bovine gamma-globulin (BGG), etc. Alternatively, synthetic poly(amino acids) may be utilized.

The immunogenic carrier can also be a polysaccharide, which is a high molecular weight polymer built up by repeated condensations of monosaccharides. Examples of polysaccharides are starches, glycogen, cellulose, carbohydrate gums such as gum arabic, agar, and so forth. The polysaccharide can also contain polyamino acid residues and/or lipid residues.

The immunogenic carrier can also be a poly(nucleic acid) either alone or conjugated to one of the above mentioned poly(amino acids) or polysaccharides.

The immunogenic carrier can also be a particle. The particles are generally at least about 0.02 microns (μm) and not more than about 100 μm, and usually about 0.05 μm to 10 μm in diameter. The particle can be organic or inorganic, swellable or non-swellable, porous or non-porous, optionally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "analyte" refers to any substance or group of substances, the presence or amount of which is to be determined. As used herein, the term analyte subsumes the term "antigen," which refers to any compound that can bind to an antibody. Furthermore, as used herein, the term analyte refers to all manner of chemical substances, including but not limited to conjugates, immunogens, drugs, drug derivatives, hormones, proteins, antigens, oligonucleotides and the like. Representative ecstasy-class analytes include but are not limited to MDA, MDMA, MDEA, MDPA, BDB, MBDB and the like.

The term "derivative" refers to a chemical compound or molecule made from a parent compound by one or more chemical reactions.

The term "analyte analog" refers to any substance or group of substances, such as may be employed in a competitive immunoassay, which behaves similarly to an analyte with respect to binding affinity to an antibody. Representative analyte analogs include drugs and isomers thereof, drug derivatives, hormones, polypeptides, nucleotides and the like.

The phrase "detecting an analyte" refers to any quantitative, semi-quantitative or qualitative method, as well as to all other methods for determining an analyte in general, and an ecstasy-class drug in particular. For example, a method that merely detects the presence or absence of an ecstasy-class drug in a sample lies within the scope of the present invention, as do methods that provide data as to the amount or concentration of the drug in the sample. The terms detecting, determining, identifying and the like are used synonymously herein, and all are within the scope of the present invention.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for ecstasy-class compounds. The kit may further comprise ligands of the analyte and calibration and control materials. The reagents may remain in liquid form or may be lyophilized.

The phrase "calibration and control materials" refers to any standard or reference material containing a known amount of an analyte to be measured. A sample suspected of containing an analyte and the corresponding calibration material are assayed under similar conditions. The concentration of analyte is calculated by comparing the results obtained for the unknown specimen with the results obtained for the standard. This is commonly done by constructing a calibration curve.

The term "alkyl group" refers to any straight, branched, cyclic, acyclic, saturated or unsaturated carbon chain. Representative alkyl groups include alkanes, alkenes, alkynes, cycloalkanes, cycloalkenes, cycloalkynes, aryls, and the like, and combinations thereof.

The phrase "optionally substituted" refers to the optional attachment of one or more substituents onto an alkyl group.

The term "leaving group" refers to any chemical moiety of a substrate that can be displaced by a reagent reacted therewith. Suitable leaving groups include, but are not limited to, halides, mesylates, tosylates, alkoxys, quaternary ammonium salts, and the like. Preferred leaving groups for use in accordance with the presently preferred embodiments are provided by activated esters, e.g., trifluoroethoxy esters, N-hydroxysuccinimide esters, p-nitrophenyl esters, pentafluorophenyl esters, imidazolyl esters, and N-hydroxybenzotriazolyl esters, whereby the oxygen-containing portion of the ester that is attached to the carbonyl carbon is displaced in the course of the reaction.

The term "protecting group" refers to any moiety that is attached to a reactive atom or center in order to alter its usual reactivity. Suitable protecting groups include but are not limited to those described in the treatise entitled *Protective Groups in Organic Synthesis, 3rd Edition* by Theodora W. Greene and Peter G. M. Wuts (John Wiley & Sons, Inc., New York, 1999). Various protecting groups for the nitrogen of amines are known in the art, among which trifluoroacetyl is a presently preferred nitrogen protecting group.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, urine, tears, cells, organs, tissues, bone, bone marrow, lymph, lymph nodes, synovial tissue, chondrocytes, synovial macrophages, endothelial cells, and skin.

A compound embodying features of the present invention is useful as a intermediate, hapten or immunogen in the production of antibodies specific for ecstasy-class drugs. A first series of compounds embodying features of the present invention has the following structure:

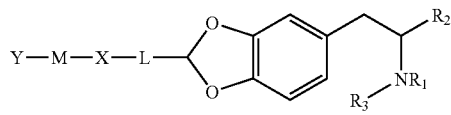

wherein L is CO or $CH_2$, X is NH or O, M is a saturated or unsaturated, aliphatic or aromatic, substituted or unsubstituted, straight or branched chain of 0-10 carbon or hetero atoms, Y is an activated functionality selected from the group consisting of active esters, isocyanates, isothiocyanates, thiols, imidoesters, anhydrides, maleimides, thiolactones, diazonium groups, and aldehydes, and $R_1$ is H, $CH_3$, $C_2H_5$, or $C_3H_7$, $R_2$ is $CH_3$ or $C_2H_5$, and $R_3$ is a protecting group or H.

A second series of compounds embodying features of the present invention has the following structure:

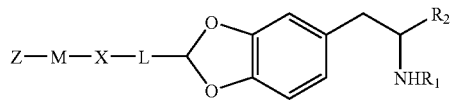

where $R_1$ is H, $CH_3$, $C_2H_5$, or $C_3H_7$, $R_2$ is $CH_3$ or $C_2H_5$, Z is a carrier molecule, L is CO or $CH_2$, and X is NH or O, M is a saturated or unsaturated, aliphatic or aromatic, substituted or unsubstituted, straight or branched chain of 0-10 carbon or hetero atoms.

The synthetic scheme for immunogens and the screening conjugates of MDMA, MDEA, MDA, MBDB, and BDB are illustrated in FIGS. 1-13. In these figures, the reactions are carried out in sequential order. Underlined, boldface numbers refer to the corresponding structure in the drawings.

In general, reductive amination of 3,4-dimethoxyphenyl acetone (see FIG. 1) is carried out by using an appropriate amine (ammonia, methylamine, or ethylamine) in the presence of a reducing agent, preferably sodium borohydride or sodium cyanoborohydride, at a temperature from 0° C. to 25° C. to give the desired 3,4-dimethoxyphenyl propylamine (1A). The latter intermediate is then demethylated to give the 3,4-dihydroxyphenyl propylamine. Typically, demethylation of phenolic derivatives is carried out by reaction with boron tribromide in dichloromethane at −70° C. to room temperature. A variety of demethylation reactions are known in the art, for example, trimethylsilyl-iodide, sodium thioethoxide, potassium thiophenoxide, sodium cyanide in DMSO, aluminium tribromide in ethanethiol, and hydrobromic acid (Greene, T. and Wuts, P., "Protective groups in organic synthesis", 2nd edition, Wiley-Intersciences, 1991). Preferably the demethylation of the 3,4-dimethoxyphenyl propylamine derivative (1A) is carried out in the presence of 48% HBr under reflux conditions for 3-4 hours to give 1B. The amino group of the 3,4-dihydroxyphenyl propylamine 1B is then protected.

Protection of amino group in the presence of free phenolic hydroxy groups is known in the art. These reactions can be done by a proper choice of protecting group and reaction conditions. An example of an N-protecting group removed under mildly basic conditions is fluorenylmethyloxycarbonyl (FMOC). An example of an N-protecting group easily removed with acid is t-butyloxycarbonyl (BOC). A preferred protection for the amino group of the 3,4-dihydroxyphenyl propylamine derivative (1B) is BOC in this reaction sequence. Selective protection of the amino group of the 3,4-dihydroxyphenyl propylamine derivative (1B) as BOC in the presence of free phenolic groups is preferentially carried out by reaction with di-t-butyl-dicarbonate in aqueous THF containing a mild base, preferably sodium bicarbonate. The 3,4-dihydroxyphenyl N-BOC propylamine intermediate (1C) is then converted to a 3,4-methylenedioxyphenyl N-BOC propylamine derivative (1D) by alkylation reaction with an alkyl dihaloacetate (RCOOCHX2, where X=I, Br, or Cl, and R=lower alkyl with 1 to 5 carbon atoms), preferably ethyl dibromoacetate in the presence of a base and a dipolar aprotic solvent, and most preferably potassium carbonate in DMF under anhydrous conditions at 120° C. The ester functionality of the resultant key ethoxycarbonyl substituted 3,4-methylenedioxyphenyl N-BOC-propylamine derivative (1D) can be modified to introduce various functional groups through different linker attachments. Most preferably, the latter ethyl ester is converted first to an amide (1E) with ammonia in methanol under conditions well known in the art. This is followed by reducing the amide (1E) with a reducing agent, preferably lithium aluminium hydride, at −70° C. to room temperature. The amino group of the resultant aminomethyl 3,4-methylenedioxyphenyl N-BOC propylamine derivative (1F) is amenable to acylation reactions with a wide variety of carboxyl activated linker extensions or labels that are well known to those skilled in the art. Linker extension is often performed to generate a terminal activated group. For example, in one preferred embodiment, an aminomethyl modified 3,4-methylenedioxyphenyl N-BOC propylamine derivative (1F) was reacted with commercially available linkers of the maleimido alkanoic acid N-hydroxysuccinimide ester type to generate terminal maleimido groups for subsequent conjugation to thiol groups on polypeptides and labels (see FIG. 7). The N-BOC group of the resultant maleimido derivative (2N) is deprotected in the presence of trifluoroacetic acid. The deprotected maleimido adduct (2O) is then ready for reaction with thiol-containing proteins to form thiol ether conjugates. Thiol-groups on proteins can be derived from native cysteine residues or can be introduced through reaction with thiolating reagents. Some examples of thiolating reagents are 2-iminothiolane (2-IT), succinimidyl acetylthiopropionate (SATP), and succinimidyl 2-pyridyldithiopropionate (SPDP). The incipient thiol group is available after proper deprotection of SATP (or SPDP) modified protein for conjugation to a maleimido derivative (2O). Alternatively, an amino-terminated linker of an aminomethyl substituted 3,4-methylenedioxyphenyl derivative (1F) is extended with a heterobifunctional thiolating agent which reacts to form an amide bond at one end and a free or protected thiol at the other end and is subsequently used to conjugate with a maleimido modified protein. Alternatively, linker extension using a homobifunctional linker such as N-hydroxysuccinimide ester of a biscarboxylic acid such as terephthalic acid can be used to generate an activated ester in a single step by reaction with the aforementioned amino derivative. For a good treatise on the subject of linkers, the reader is referred to Hermanson, Greg T., "Bioconjugate Techniques", Academic Press Inc., 1996. In yet another preferred embodiment for linker extension, succinylation of the amino group of aminomethyl 3,4-methylenedioxyphenyl N-trifluoroacetyl propylamine derivative (1J) is carried out with succinic anhydride in the presence of a base (see FIG. 2). Preferred bases are pyridine, triethylamine, diisopropylethylamine, 4-dimethylaminopyridine, and most preferably either triethylamine, 4-dimethylaminopyridine, or a combination of both of the aforementioned bases. The reaction is carried out at 40-60° C. in an anhydrous solvent such as ethyl acetate, THF, 1,2-dichloroethane, preferably 1,2-dichloroethane. The resulting acid is activated by conversion to an active ester, preferably an N-hydroxysuccinimide ester, by reaction with a carbodiimide, preferably 1-ethyl-3-(3-dimethylaminopropyl)-carbodiimide (EDC), and N-hydroxysuccinimide. This activated ester is used to conjugate to synthetic polypeptides or aminodextran following a standard procedure known in the art. The deprotection of the N-trifluoroacetyl group of the hapten moiety in the conjugate is performed by treatment with base, preferably 10% ammonium hydroxide or pH 11 potassium carbonate. Alternatively, an acid labile protecting group such as BOC can be used in the same sequence and removed from the conjugate by treatment with trifluoroacetic acid.

For the preparation of protein conjugates, a base sensitive protecting group on the hapten derivative is preferred for the sake of stability of protein. Acidic conditions are known to denature protein. A variety of base sensitive protecting groups can be selected, the preferred being a trifluoroacetyl group. A BOC methylenedioxyphenyl amino derivative (1F) is protected with a carbobenzoxy (CBz) group. The CBz protection of the amino functionality is known in the art using the reagent CBz chloride at a temperature 0° C. to 25° C., preferably at room temperature. This is followed by deprotection of the BOC group under acidic conditions, preferably with trifluoroacetic acid. The free amino group (primary or secondary amine, 1H or 2H) is protected as trifluoroacetamide. The reaction is well known in the art using any trifluoroacetylating agent, ethyl trifluoroacetate, or trifluoroacetic anhydride, preferably using trifluoroacetic anhydride. The CBz protecting group of the trifluoroacetamide compound (1I) is deprotected under hydrogenation conditions using 10% Pd—C under atmospheric pressure. The free amino group (1J) is extended to a carboxyl group through a succinylation reaction as described earlier. The activation of the carboxyl group (1K) is accomplished by an activation step using a carbodiimide such as dicyclohexylcarbodiimide (DCC) or EDC, preferably EDC in the presence of N-hydroxysuccinimide. Conjugation to protein provides the protected immunogen and screening conjugates. The deprotection of the trifluoroacetamido group of the protein conjugates is accomplished by treatment with aqueous base, preferably by dialysing against aqueous potassium carbonate (pH 11) or 10% ammonium hydroxide (pH 11.5) to provide an immunogen (1P) and a BSA screening conjugate (1O).

Conversion of the ester group of ethoxycarbonyl substituted 3,4-methylenedioxy phenyl N-BOC-propylamine (1D) to its hydrolyzed acid product (1M), followed by extension through a linking group using an amide linkage, can also be a route to prepare an activated ester for conjugation to a protein. Alternatively, the ester functionality (1D) can be reduced by a reducing agent, preferably lithium aluminium hydride, to give an alcohol (1N) which can be extended through an ester, urethane, or ether linkage and similarly, as described earlier, converted to an active ester for conjugation to protein.

Figure 12:
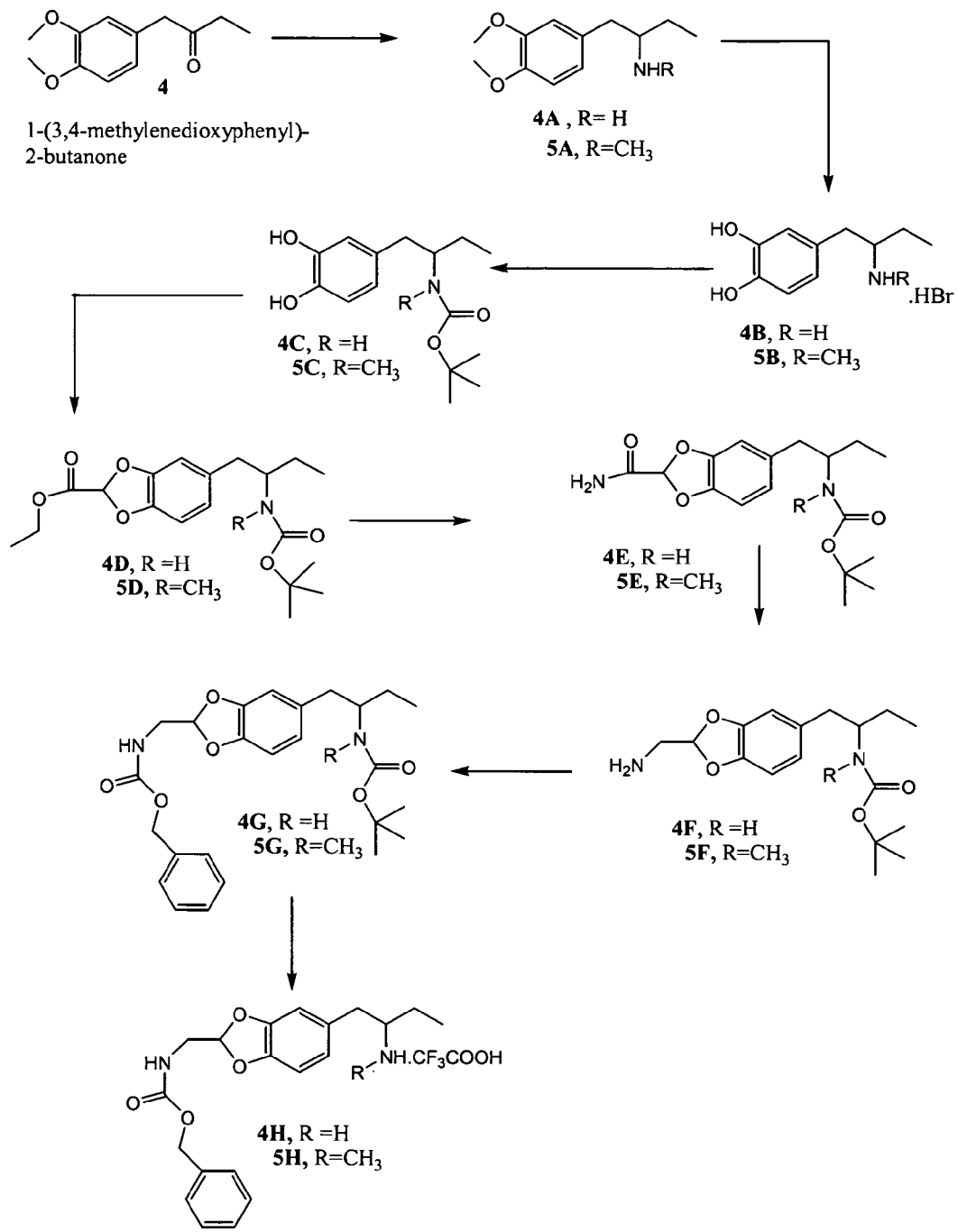
FIG. 12 is a schematic representation of a synthetic method for carbobenzoxy protected BDB (4H) and MBDB (5H) derivatives.
Figure 13:
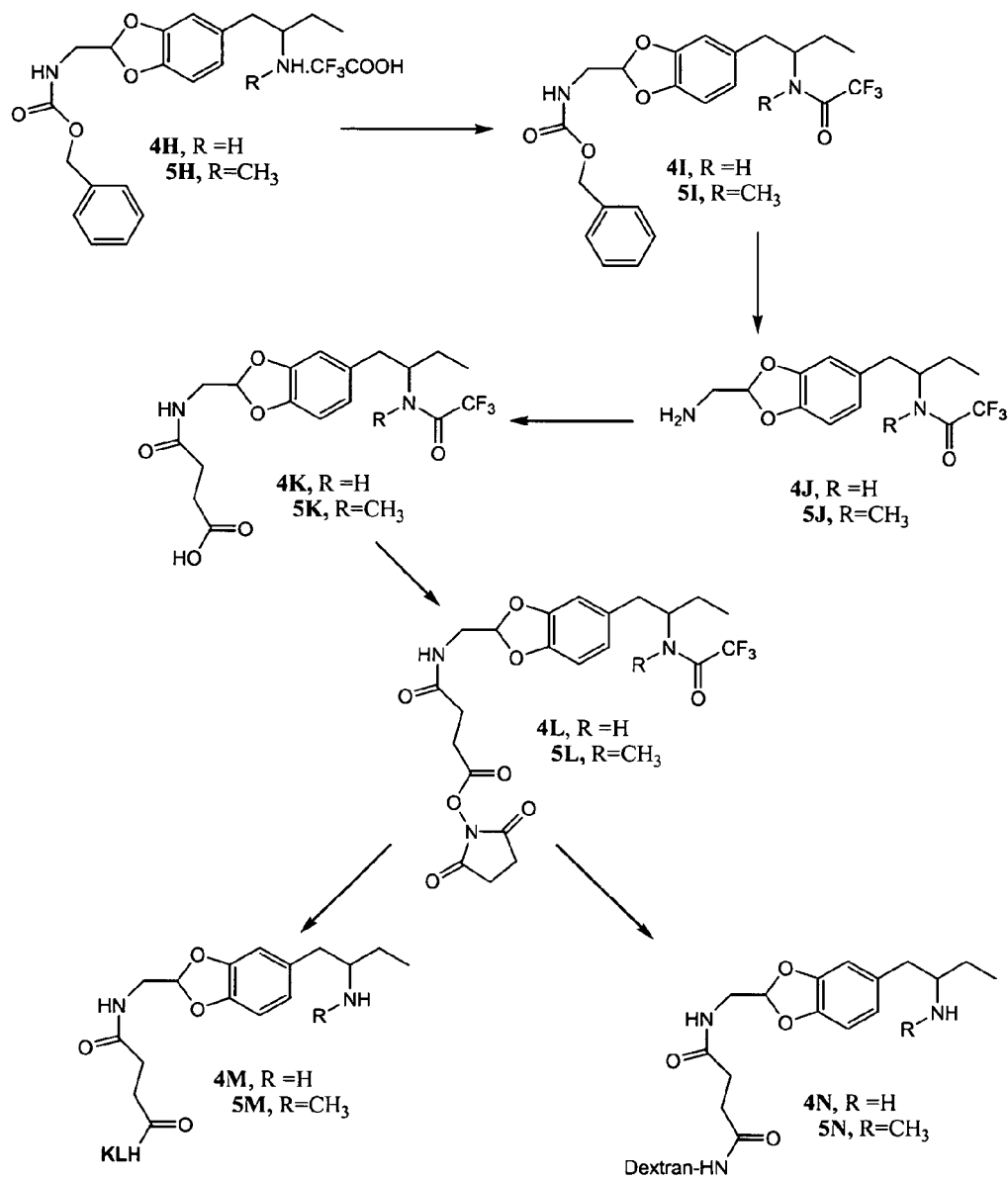
FIG. 13 is a schematic representation of a synthetic method for KLH and aminodextran conjugates of BDB (4M and 4N) and MBDB (5M and 5N) derivatives.

Analogous methods as described for MDMA derivatives (FIGS. 1-3) are used to synthesize MDEA derivatives and conjugates (FIGS. 4-9), MDA derivatives and conjugates (FIGS. 10 and 11), and BDB or MBDB derivatives and conjugates (FIGS. 12 and 13).

An unforeseen result of the work described herein is that in several cases, antibodies with much higher binding to structurally related molecules than for the drug corresponding to the immunogen were obtained. From the fusions in which MDMA-KLH was used as an immunogen, clones were obtained which showed a very significant preference for MDEA over reactivity to MDMA. The clone MDMA 8.2 showed nearly a 89-fold preference for MDEA over MDMA. It was unexpected that the presence of an ethyl group would confer such a high cross-reactivity toward an antibody raised to a molecule with a methyl group at that same position.

Another surprising antibody obtained from an MDMA-KLH fusion was MDMA 6.1 in which unexpectedly high cross-reactivities toward d-methamphetamine and MBDB were observed. The former drug lacks the methylenedioxy portion of the immunogen structure, and the latter drug has an ethyl group in place of a methyl in the immunogen. Although this may seem the same as what was found for MDMA 8.2, it is not, as the substitution is in a significantly different position.

Also, the use of an MDEA immunogen was found to give rise to unexpected antibodies. Clone MDEA 2.2 showed a 4-fold preference for MDMA and a 44-fold preference for MBDB over the immunizing hapten MDEA. Both reactivities were unexpected based on the structural differences of these drugs.

Specific Embodiments

In the examples that follow, boldface numbers refer to the corresponding structure in the drawings.

EXAMPLE 1

[2-(3,4-dimethoxy-phenyl)-1-methyl-ethyl]-methyl-amine (1A)

A solution of 15.1 g (78 mmol) of (3,4-dimethoxyphenyl) acetone (1) in 102 mL of methanol was cooled to 4° C. and was treated with 35 mL of 40% aqueous methylamine. To the reaction mixture, 3.5 g (92.5 mmol) of sodium borohydride was then added, and the temperature of the reaction was maintained at 4° C. The reaction mixture was allowed to stir for an additional 30 minutes, then concentrated under reduced pressure. To the residue, 60 mL of water was added, and the resulting reaction mixture was acidified to pH 1 using 6N HCl. The aqueous layer was extracted with 5×50 mL of dichloromethane, and the pH was adjusted to pH 13 using 6N NaOH. The aqueous layer was extracted with 4×75 mL of dichloromethane. The organic layers were combined, dried and concentrated to give 15 g (72 mmol, 92%) of 1A as a colorless oil (M+H, 210).

EXAMPLE 2

4-(2-methylamino-propyl)-benzene-1,2-diol, Compound with Hydrobromic Acid Salt (1B)

A solution of 2 g (9.5 mmol) of 1A in 20 mL of 48% HBr was heated to reflux under argon atmosphere for 3.5 hours and concentrated under reduced pressure to give 1B as a dark brown oil. This was used in the next step without further purification.

EXAMPLE 3

[2-(3,4-dihydroxy-phenyl)-1-methyl-ethyl]-methyl-carbamic Acid Tert-butyl Ester (1C)

To all of 1B from the above reaction mixture was added 40 mL of 50% tetrahydrofuran (THF) in water. To the reaction mixture, 2.0 g of sodium bicarbonate was then added. A solution of 2 g (9.2 mmol) of di-t-butyldicarbonate in 10 mL of THF was added dropwise with stirring over a period of 30 minutes, and the mixture was allowed to stir for 12 hours. An additional 500 mg (2.29 mmol) of di-t-butyl-dicarbonate in 10 mL of THF was then added to the reaction mixture over a period of 40 minutes, and the reaction was allowed to stir for an additional 20 minutes before concentrating under reduced pressure. To the residue, 50 mL of water was added, and the resulting mixture was extracted with 4×50 mL of ethyl acetate. Organic layers were combined, dried (anhydrous $Na_2SO_4$) and concentrated to dryness under reduced pressure. The residue was purified by flash column silica gel chromatography using 30% ethyl acetate in hexane to give 2.5 g (8.8 mmol, 93% from 1A) of 1C as a colorless oil (M+Na, 304).

EXAMPLE 4

5-[2-(tert-butoxycarbonyl-methyl-amino)-propyl]-benzo[1,3]dioxole-2-carboxylic Acid Ethyl Ester (1D)

To 2.5 g (8.8 mmol) of 1C was added 20 mL of anhydrous N, N-dimethylformamide (DMF) followed by 3.68 g (26 mmol) of anhydrous $K_2CO_3$ and 3 mL (23 mmol) of ethyl dibromoacetate. The reaction mixture was heated to 100° C. for 4.5 hours and then allowed to cool to room temperature. This was concentrated to dryness under reduced pressure, and 50 mL of water was added to the residue. The mixture was adjusted to pH 3 using 1N HCl and extracted with 4×50 mL of dichloromethane. Organic layers were combined, dried (anhydrous $Na_2SO_4$), and concentrated to dryness. The residue was purified by flash column silica gel chromatography using 15% ethyl acetate in hexane to give 1.1 g (3.01 mmol, 34%) of 1D as a colorless oil (M+Na, 388).

EXAMPLE 5

[2-(2-hydroxymethyl-benzo[1,3]dioxo-5-yl)-1-methyl-ethyl]-methyl-carbamic Acid Tert-butyl Ester (1N)

A mixture of 313 mg (8.24 mmol) of lithium aluminium hydride in 4 mL of freshly distilled THF was cooled to −25° C. to −35° C. To the reaction mixture was added a solution of 630 mg (1.72 mmol) of 1D in 10 mL of THF dropwise for a period of 20 minutes. The mixture was allowed to stir at −30° to −40° C. for 20 minutes and quenched with 10 mL of ethyl acetate. This was filtered through CELITE, and the filtrate was concentrated to dryness. The residue was purified by silica gel chromatography using ethyl acetate as eluent to give 480 mg (1.48 mmol, 86%) of 1N as a thick colorless gum (M+Na, 346).

EXAMPLE 6

5-[2-(tert-butoxycarbonyl-methyl-amino)-propyl]-benzo[1,3]dioxole-2-carboxylic Acid (1M)

To a mixture of 21 mg (0.06 mmol) of 1D in 0.5 mL of THF, 0.5 mL of methanol, and 1 mL of water was added 50 mg (1.19 mmol) of lithium hydroxide monohydrate as solid. The reaction mixture was allowed to stir at room temperature for 2.5 hours and concentrated to dryness. To the residue, 10 mL of water was added, and pH of the resulting mixture was adjusted to 2 using phosphoric acid. This was extracted with 3×35 mL of ethyl acetate. Organic layers were combined, dried (anhydrous $Na_2SO_4$) and concentrated to dryness to give 10 mg (0.029 mmol, 53%) of 1M (M+Na, 360).

EXAMPLE 7

[2-(2-carbamoyl-benzo[1,3]dioxol-5-yl)-1-methyl-carbamic Acid Tert-butyl Ester (1E)

A solution of 0.85 g (2.32 mmol) of 1D was prepared in 10 mL of anhydrous methanol. Anhydrous ammonia gas was then bubbled through the reaction mixture for 60 minutes and the resulting reaction mixture was concentrated under reduced pressure to dryness. The residue was purified by flash column silica gel chromatography using 15% hexane in ethyl acetate to give 0.76 g (2.25 mmol, 97%) of 1E as a colorless oil (M+H, 359).

EXAMPLE 8

[2-(2-aminomethyl-benzo[1,3]dioxol-5-yl)-1-methyl-ethyl]-methyl-carbamic Acid Tert-butyl Ester (1F)

To 500 mg of lithium aluminium hydride (13.2 mmol) was added 10 mL of freshly distilled THF, and the reaction flask was cooled to −30° C. A solution of 0.75 g (2.22 mmol) of 1E in 14 mL of freshly distilled THF was added dropwise, and the reaction mixture was allowed to stir at −30° C. for 1.5 hours and at 0° C. for 1.5 hours. The reaction mixture was allowed to warm up to room temperature and allowed to stir at room temperature for 1.5 hours. To the reaction mixture 50 mL of ethyl acetate was added, and the mixture was filtered through CELITE (Celite Corporation). The filtrate was concentrated to dryness and 50 mL of water were added. The dry residue was extracted with 4×50 mL of ethyl acetate. Organic layers were combined, dried (anhydrous $Na_2SO_4$) and concentrated. The residue was purified by flash silica gel column chromatography using ethyl acetate as solvent to give 0.31 g (43%, 0.96 mmol) of 1F as a thick colorless oil (M+Na, 345).

EXAMPLE 9

[2-[2-(benzyloxycarbonylamino-methyl)-benzo[1,3] dioxol-5-yl]-1-methyl-ethyl}-methyl-carbamic Acid Tert-butyl Ester (1G)

To a solution of 0.31 g (0.96 mmol) of 1F in 5 mL of dichloromethane was added 0.2 mL (1.14 mmol) of N,N-diisopropylethylamine and 10 mg (0.08 mmol) of 4-dimethylaminopyridine (4-DMAP) followed by 0.15 mL of benzyl chloroformate (1.04 mmol) at room temperature. The mixture was allowed to stir for 1 hours and concentrated to dryness under reduced pressure. The residue was purified by silica gel flash column chromatography using 40% ethyl acetate in hexane to give 0.41 g (0.89 mmol, 94%) of 1G as a thick colorless gum (M+Na, 479).

EXAMPLE 10

[5-(2-methylamino-propyl)-benzo[1,3]dioxol-2-yl methyl]-carbamic Acid Benzyl Ester Compound with Trifluoroacetic Acid (1H)

To a solution of 0.41 g (0.89 mmol) of 1G in 2 mL of dichloromethane was added 2 mL of trifluoroacetic acid. The resulting solution was allowed to stir at room temperature for 90 minutes and concentrated under reduced pressure. The residue was purified by silica gel flash column chromatography using 20% methanol in ethyl acetate to give 0.29 g (0.64 mmol, 69%) of 1H as a colorless thick gum (M+Na, 357).

EXAMPLE 11

(5-{2-[methyl-(2,2,2-trifluoro-acetyl)-amino]-propyl}-benzo[1,3]dioxol-2-ylmethyl)-carbamic Acid Benzyl Ester (1I)

A solution of 299 mg (0.64 mmol) of 1H in 5 mL of dichloromethane was cooled to 0° C. To the reaction mixture was added 0.25 mL (1.43 mmol) of diisopropylethylamine, 10 mg (0.08 mmol) of 4-DMAP followed by 0.3 mL (2.12 mmol) of trifluoroacetic anhydride at 0° C. The mixture was allowed to warm up to room temperature and stirred for 1 hour. The reaction mixture was concentrated under reduced pressure, and the residue was purified by silica gel flash column chromatography using 20% ethyl acetate in hexane to give 150 mg (0.33 mmol, 52%) of 1I as a colorless oil (M+Na 453).

EXAMPLE 12

N-[2-(2-aminomethyl-benzo[1,3]dioxol-5-yl)-1-methyl-ethyl]-2,2,2-trifluoro-N-methyl-acetamide (1J)

To a solution of 150 mg (0.33 mmol) of 1I in 10 ml of methanol was added 24 mg of 10% Pd—C, and the mixture was hydrogenated for 4 hours at room temperature under atmospheric pressure using a hydrogen filled balloon. The reaction mixture was filtered through CELITE and the residue was washed with 20 mL of methanol. The filtrates were combined and concentrated to dryness under reduced pressure. The residue was purified by silica gel flash column chromatography using 10% methanol in ethyl acetate to give 95 mg (0.29 mmol, 86%) of 1J as a colorless oil (M+H, 319).

EXAMPLE 13

N-(5-{2-[methyl-(2,2,2-trifluoro-acetyl)-amino]-propyl}-benzo[1,3]dioxol-2-yl methyl-succinamic Acid (1K)

To a solution of 680 mg (2.13 mmol) of 1J in 20 mL of methanol was added 0.6 mL (3.4 mmol) of diisopropylethylamine followed by 10 mg (0.08 mml) of 4-DMAP, and the reaction mixture was cooled to 0° C. To the reaction mixture 800 mg (7.9 mmol) of succinic anhydride was added and was warmed up to room temperature. The reaction mixture was allowed to stir at room temperature for 1.5 hours and concentrated under reduced pressure. This was purified by silica gel flash column chromatography using ethylacetate as solvent to give 400 mg (0.95 mmol, 45%) of 1K as a white gummy solid (M+H, 419).

EXAMPLE 14

N-(5-{2-[methyl-(2,2,2-trifluoro-acetyl)-amino]-propyl}-benzo[1,3]dioxol-2-yl methyl)-succinamic Acid 2,5-dioxo-pyrrolin-1-yl Ester (1L)

To a solution of 400 mg (0.27 mmol) of 1K in 40 mL of dichloromethane was added 273 mg (2.37 mmol) of N-hydroxysuccinimide followed by 440 mg (2.29 mmol) of 1-ethyl-3-(3-dimethylaminopropyl)-carbodiimide. The mixture was allowed to stir at room temperature under argon atmosphere for 11 hours. The reaction mixture was washed with 2×15 mL of water and 4×15 mL of saturated sodium bicarbonate followed by 15 mL of water. The organic layer was dried (anhydrous $Na_2SO_4$) and concentrated to dryness under reduced pressure. The residue was purified by flash column chromatography to give 250 mg (0.48 mmol, 51%) of 1L as a thick gum (M+H, 516).

EXAMPLE 15

MDMA Immunogen (1P)

A solution of 173 mg of keyhole limpet hemocyanin in 7 ml of 50 mM potassium phosphate (pH 7.5) was cooled in an ice-bath. To the solution were added 10.5 mL of dimethylsulfoxide (DMSO) dropwise, and the reaction temperature was maintained below room temperature. To the protein solution was added a solution of 40.2 mg of 1L in 1.5 mL of DMF dropwise. The mixture was allowed to stir at room temperature 18 hours. The resulting conjugate was placed in a dialysis tube (10,000 MW cut-off) and dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature. The trifluoroacetamido group of the conjugate was deprotected by dialysis of the resulting conjugate against 10% ammonium hydroxide for 3 days (1 L each for approximately 24 hours each), followed by 6 changes with 50 mM potassium phosphate (pH 7.5) at 4° C. (1 L each for at least 6 hours each). The protein concentration was determined to be 2.9 mg/mL using BioRad Coomassie blue protein assay (Bradford, M., *Anal. Biochem.* 72:248, 1976). A total of 34 mL of the conjugate was obtained. The extent of available lysine modification was determined to be 72% by the 2,4,6-trinitrobenzene sulfonate (TNBS) method (Habeeb AFSA, *Anal. Biochem.* 14:328-34, 1988).

EXAMPLE 16

MDMA-BSA Conjugate (1O)

A solution of 800 mg of bovine serum albumin (BSA) in 8 mL of 50 mM potassium phosphate (pH 7.5) was cooled in an ice-bath. To the solution was added 12 mL of DMSO dropwise, and the reaction mixture was maintained below room temperature. To the protein solution was added a solution of 15 mg of MDMA derivative (1L) in 1 mL of anhydrous DMF dropwise. The reaction mixture was allowed to stir at room temperature 48 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature. The trifluoroacetamido group of the conjugate was deprotected by dialysis of the resulting conjugate against 10% ammonium hydroxide for 3 days (1 L each for approximately 24 hours each), followed by 6 changes with 50 mM potassium phosphate (pH 7.5) at 4° C. (1 L each for at least 6 hours). The protein concentration was determined to be 6.8 mg/mL using BioRad Coomassie blue protein assay (Bradford, M., *Anal. Biochem.* 72:248, 1976). A total of 38 mL of the conjugate was obtained.

EXAMPLE 17

[2-(3,4-dimethoxy-phenyl)-1-methyl-ethyl]-ethyl amine (2A)

A solution of 10 g (51.4 mmol) of 3,4-dimethoxyphenylacetone in 50 mL of methanol was cooled to 0° C. and was treated with 50 mL of 2M solution of ethylamine in methanol. To the reaction mixture 11.5 g (0.183 mmol) of sodium cyanoborohydride was added, and the pH of the reaction mixture was adjusted to 6.5-7 by adding glacial acetic acid. The mixture was allowed to stir at room temperature for 4 days. This was concentrated under reduced pressure, and 150 mL of water was added. The pH of the resulting solution was adjusted to 1 using 6 N HCl. This was extracted with 4×150 mL of ether and the organic layers were discarded. The pH of the aqueous layer was adjusted to 14, and the solution was extracted with 6×100 mL of chloroform. The organic layers were combined, dried ($Na_2SO_4$) and concentrated to dryness to give 10.6 g (47.4 mmol, 92%) of 2A as a pale yellow oil (M+H, 224).

EXAMPLE 18

4-(2-ethylamino-propyl)-benzene-1,2-diol Compound with Hydrobromic Acid Salt (2B)

A solution of 1.1 g (4.92 mmol) of 2A in 10 mL of 48% HBr was heated to reflux under argon atmosphere for 3.5 hours and then concentrated to dryness under reduced pressure. To this was added 50 mL of dichloromethane and concentrated to dryness under reduced pressure to give crude 2B as a dark brown powder (M+Na, 318).

EXAMPLE 19

[2-(3,4-dihydroxy-phenyl)-1-methyl-ethyl]-ethyl-carbamic Acid Tert -butyl Ester (2C)

To all of 2B from the above reaction mixture was added 30 mL of 50% THF in water. To the reaction mixture 1.1 g of sodium bicarbonate was added as a solid followed by 1.35 g (6.18 mmol) of di-t-butyl dicarbonate in 7 mL of THF dropwise over a period of 30 minutes. The reaction mixture was allowed to stir at room temperature for 18 hours, then concentrated under reduced pressure. This was diluted with 50 mL of water and the pH of the solution was adjusted to 5. The aqueous layer was extracted with 3×100 mL of ethyl acetate. The organic layers were combined, dried (anhydrous $Na_2SO_4$) and concentrated to dryness. The residue was purified by silica gel column chromatography using 30% ethyl acetate in hexane to give 764 mg (2.58 mmol, 53% from 2A) of 2C as a clear gum (M+Na, 318).

EXAMPLE 20

5-[2-(tert-butoxycarbonyl-ethyl-amino)-propyl]-benzo[1,3]dioxole-2-carboxylic Acid Ethyl Ester (2D)

To 2 g (6.7 mmol) of 2C was added 40 mL of anhydrous DMF followed by 3.5 g (25 mmol) of anhydrous $K_2CO_3$, 5 g of 3 A° molecular sieves and 3.2 mL (25 mmol) of ethyl dibromoacetate. The reaction mixture was heated at 120° C. for 3 hours under argon atmosphere and then concentrated under reduced pressure. To the residue 75 mL of ethyl acetate were added and filtered. To the filtrate 75 mL of water were added and transferred to a separatory funnel. The organic layer was separated, and the aqueous layer was extracted with 5×75 mL of ethyl acetate. All the organic layers were combined, dried (anhydrous $Na_2SO_4$), and concentrated to dryness. The residue was purified by silica gel column chromatography using 10% ethyl acetate in hexane to give 954 mg (5.3 mmol, 37%) of 2D as a colorless gum (M+Na, 402).

EXAMPLE 21

[2-(2-carbamoyl-benzo[1,3]dioxol-5-yl)-1-methyl-ethyl]-ethyl-carbamic Acid Tert-butyl Ester (2E)

To 2.04 g (5.37 mmol) of 2D was added 30 mL of anhydrous methanol, and ammonia gas was passed through the solution for 1 hour at room temperature. The mixture was concentrated to dryness and the residue purified by silica gel column chromatography using 30% hexane in ethyl acetate to give 1.8 g (5.13 mmol, 96%) of 2E as a colorless gum (M+Na, 373).

EXAMPLE 22

[2-(2-aminomethyl-benzo[1,3]dioxol-5-yl)-1-methyl-ethyl]-ethyl-carbamic Acid Tert-butyl Ester (2F)

A flask containing 20 mL of freshly distilled THF was cooled to −60° C., and 615 mg (16.2 mmol) of lithium aluminun hydride (LAH) was added To the reaction mixture, a solution of 1.8 g (5.13 mmol) 2E in 20 mL of freshly distilled THF was added dropwise under argon atmosphere. The reaction mixture was allowed to stir at −60° C. for 20 minutes, 45 minutes at 0° C. and 2 hours at room temperature. The reaction was quenched with 430 μL of 15% NaOH and 3 mL of water and allowed to stir at room temperature for 10 minutes. The resulting solution was filtered through CELITE and the residue was washed with 100 mL of THF. The filtrate was concentrated to dryness under reduced pressure and purified by silica gel column chromatography using ethyl acetate as eluent to give 1.3 g (3.86 mmol, 75%) of 2F as a colorless gum (M+Na, 359).

EXAMPLE 23

[2-[2-(benzyloxycarbonylamino-methyl)-benzo[1,3]dioxol-5-yl]-1-methyl-ethyl}-ethyl-carbamic Acid Tert-butyl Ester (2G)

To a solution of 1.3 g (3.86 mmol) of 2G in 40 mL of dichloromethane (distilled over $CaH_2$) was added 1.52 mL (8.6 mmol) of diisopropylethylamine, 30 mg (0.24 mmol) of 4-DMAP and 1.14 mL (7.9 mmol) of benzyl chloroformate. The reaction mixture was allowed to stir at room temperature for 3 hours under argon atmosphere and concentrated to dryness under reduced pressure. The residue was purified by silica gel column chromatography using 20% ethyl acetate in hexane to give 1.58 g (3.3 mmol, 71%) of 2G as a colorless gum (M+Na, 493).

EXAMPLE 24

[5-(2-ethylamino-propyl)-benzo[1,3]dioxol-2-ylmethyl]-carbamic Acid Benzyl Ester Compound with Trifluoroacetic Acid (2H)

To a solution of 1.58 g (3.3 mmol) of 2G in 10 mL of dichloromethane (distilled over $CaH_2$) was added trifluoroacetic acid at room temperature, and the mixture was allowed to stir at room temperature for 30 minutes. The resulting reaction mixture was concentrated under reduced pressure to dryness and purified by silica gel column chromatography to give 1.6 g (3.3 mmol, 98%) of 2H as a colorless gum (M+H, 371).

EXAMPLE 25

(5-{2-[ethyl-(2,2,2-trifluoro-acetyl)-amino]-propyl}-benzo[1,3]dioxol-2-ylmethyl)-carbamic Acid Benzyl Ester (2I)

To 1.6 g (3.3 mmol) of 2H was added 18 mL of anhydrous DMF and cooled to −10° C. To the solution was added 3.0 mL (21 mmol) of trifluoroacetic anhydride, and the reaction mixture was allowed to stir at −10° C. for 3 hours under argon atmosphere. The reaction mixture was then allowed to warm up to room temperature and concentrated to dryness under reduced pressure. The residue was purified by silica gel column chromatography using 30% ethyl acetate in hexane to give 1 g (2.2 mmol, 65%) of 2I as a colorless gum (M+H, 467).

EXAMPLE 26

N-[2-(2-aminomethyl-benzo[1,3]dioxol-5-yl)-1-methyl-ethyl]-N-ethyl-2,2,2-trifluoro-acetamide (2J)

To 987 mg (2.1 mmol) of 2I was added 50 mL of anhydrous methanol followed by 150 mg of 10% Pd—C. This mixture was hydrogenated under atmospheric pressure 18 hours, filtered and the residue was washed with 50 mL of methanol. The combined filtrate was concentrated to dryness, and the residue was purified by silica gel column chromatography using 5% methanol in ethyl acetate to give 558 mg (1.67 mmol, 79%) of 2J as a colorless gum (M+H, 333).

EXAMPLE 27

N-(5-[2-[ethyl-(2,2,2-trifluoro-acetyl)-amino]-propyl}-benzo[1,3]dioxol-2-ylmethyl)-succinamic Acid (2K)

To a solution of 558 mg (1.67 mmol) of 2J in 25 mL of 1,2 dichloroethane was added 435 mg (4.34 mmol) of succinic anhydride, 280 μL (2 mmol) of triethylamine and 112 mg (0.91 mmol) of 4-DMAP. The reaction mixture was allowed to stir at 40° C. under argon atmosphere for 2.5 hours. It was then diluted with 50 mL of ethyl acetate and washed with 3×30 mL of 5% ammonium chloride solution. The organic layer was dried (anhydrous $Na_2SO_4$) and concentrated under reduced pressure to dryness. The residue was purified by silica gel column chromatography to give 629 mg (1.45 mmol, 86%) of 2K as a colorless gum (M+H, 433).

EXAMPLE 28

N-(5-{2-[ethyl-(2,2,2-trifluoro-acetyl)-amino]-propyl}-benzo[1,3]dioxol-2-ylmethyl)-succinamic Acid 2,5-dioxo-pyrrolidin-1-yl Ester (2L)

To 150 mg (0.34 mmol) of 2K was added 15 mL of dichloromethane (distilled over $CaH_2$) followed by 99 mg (0.86 mmol) of N-hydroxysuccinimide and 166 mg (0.86 mmol) of 1-ethyl-3-(3-dimethylaminopropyl)-carbodiimide. The reaction mixture was allowed to stir at room temperature under argon atmosphere for 18 hours. The reaction mixture was diluted with an additional 40 mL of dichloromethane and washed with 2×25 mL of water, 3×25 mL of saturated sodium bicarbonate, and 2×25 mL of water. The organic layer was dried ($Na_2SO_4$) and concentrated to dryness to give 154 mg (0.29 mmol, 84%) of 2L as a white solid (M+Na, 552).

EXAMPLE 29

5-[2-(tert-Butoxycarbonyl-ethyl-amino)-propyl]-benzo[1,3]dioxole-2-carboxylic Acid (2M)

To a solution of 50 mg (0.13 mmol) of 2D in 2 mL of 50% methanol in water was added 50 mg (1.19 mmol) of lithium hydroxide monohydrate. The mixture was allowed to stir at room temperature 18 hours and was concentrated under reduced pressure. To the residue was added 10 mL of water, and the pH was adjusted to 6 using phosphoric acid. The resulting aqueous solution was extracted with 2×25 mL of chloroform. The combined organic layers were dried ($Na_2SO_4$) and concentrated under reduced pressure to give 41 mg (0.12 mmol, 82%) of 2M as a thick colorless gum.

EXAMPLE 30

MDEA Immunogen (2U)

A solution of 188 mg of keyhole limpet hemocyanin (KLH) in 5.5 ml of 50 mM potassium phosphate (pH 7.5) was cooled in an ice-bath. To the solution were added 6 mL of dimethylsulfoxide dropwise, and the reaction temperature was maintained below room temperature. Then a solution of 54 mg (0.10 mmol) of 2L in 1.2 mL of DMF was added to the protein solution dropwise. The mixture was allowed to stir at room temperature 18 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature. The trifluoroacetamido group of the conjugate was deprotected by dialysis of the resulting conjugate against 10% ammonium hydroxide for 3 days (1 L each for approximately 24 hours each), followed by 6 changes with 50 mM potassium phosphate (pH 7.5) at 4° C. (1 L each for at least 6 hours each). The protein concentration was determined to be 2.1 mg/mL using BioRad Coomassie blue protein assay (Bradford, M., *Anal. Biochem.* 72:248, 1976). A total of 34 mL of the conjugate was obtained. The extent of available lysine modification was determined to be 60% by the TNBS method (Habeeb AFSA, *Anal. Biochem.* 14:328-34, 1988).

EXAMPLE 31

MDEA-BSA Conjugate (2T)

A solution of 500 mg of bovine serum albumin (BSA) in 6.7 mL of 50 mM potassium phosphate (pH 7.5) was cooled in an ice-bath. To the solution was added 8.5 mL of DMSO dropwise, and the reaction mixture was maintained below room temperature. To the protein solution was added a solution of 12 mg (0.022 mmol) of 2L in 1.5 mL of anhydrous DMF dropwise. The reaction mixture was allowed to stir at room temperature 48 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature. The trifluoroacetamido group of the conjugate was deprotected by dialysis of the resulting conjugate against 10% ammonium hydroxide for 3 days (1 L each for approximately 24 hours each), followed by 6 changes with 50 mM potassium phosphate (pH 7.5) at 4° C. (1 L each). The protein concentration was determined to be 7.12 mg/mL using BioRad Coomassie blue protein assay (Bradford, M., *Anal. Biochem.* 72:248,1976). A total of 45 mL of the conjugate was obtained.

EXAMPLE 32

2(2-{[3-(2,5-dioxo-2,5-dihydro-pyrrol-1-yl) -propionylamino]-methyl}-benzo[1,3]dioxol-5-yl)-1-methyl-ethyl ]-ethyl-carbamic Acid Tert-butyl Ester (2N)

A mixture containing 150 mg (0.44 mmol) of 2E and 130 mg (0.48 mmol) of succinimidyl 3-maleimido propionate in 2 mL of anhydrous DMF containing 100 µL (0.71 mmol) of triethylamine was allowed to stir at room temperature 18 hours and then concentrated under reduced pressure to dryness. The residue was purified by silica gel column chromatography using 15% methanol in chloroform to give 203 mg (0.41 mmol, 93%) of 2N as white solid (M+Na, 510).

EXAMPLE 33

3-(2,5-dioxo-2,5-dihydro-pyrrol-1-yl)-N-[5-(2-ethylamino-propyl)-benzo[1,3]dioxol-2-ylmethyl]-propionamide Compound with Trifluoro-acetic Acid (2O)

To 75 mg (0.15 mmol) of 2N in 1 mL of dichloromethane (distilled over $CaH_2$) was added 1 mL of trifluoroacetic acid. The resulting reaction mixture was allowed to stir at room temperature for 30 minutes and concentrated to dryness under reduced pressure. To the residue 5 mL of dichloromethane was added, and the resulting solution was concentrated to dryness again. The above procedure was repeated three more times to give 75 mg (0.14 mmol, 97%) of 2O as white solid (M+Na, 410).

EXAMPLE 34

MDEA-SATP-BSA Conjugate (2R)

Bovine serum albumin (0.5 g) was dissolved in 50 mL of 50 mM potassium phosphate containing 1 mM ethylenediamine tetra-acetic acid (EDTA). To the reaction mixture 1.24 mL of succinimidyl S-acetylthiopropionate (SATP) in DMSO (15 mg/mL in DMSO) was added. The reaction mixture was allowed to stand at room temperature for 1 hour. The resulting solution was then placed in a dialysis tube (10,000 MW cut-off) and dialyzed against 50 mM potassium phosphate (pH 7.5) over a period of 3 days, and the resulting BSA-SATP conjugate (2P) was stored at −20° C. for future use. The protein concentration was determined to be 9 mg/mL using BioRad Coomassie blue protein assay (Bradford, M., *Anal. Biochem.* 72:248,1976.

Removal of the acetyl protecting group from the BSA-SATP conjugate was accomplished by adding 850 µL of the following hydroxylamine-containing buffer to 5 mL of BSA-SATP (9 mg/mL): 50 mM potassium phosphate, 25 mM EDTA, 0.5 M $NH_2OH$, pH 7.2. The mixture was vortexed and allowed to stand at room temperature for 2 hours.

The resulting solution was desalted using three PD-10 columns (Amersham Pharmacia Biotech) to produce 5.5 mL of pooled protein solution. This solution was cooled to 0° C., and 4 mL of DMSO was added dropwise. A solution of 7 mg (0.014 mmol) of MDEA-maleimido derivative (2O) in 0.5 mL of DMSO was added to the protein solution. The mixture was allowed to stir at room temperature for 24 hours. To the protein solution was added 400 µL of 5 mg/mL ethyl maleimide in DMSO to quench any unreacted thiol groups, and the mixture was allowed to stir at room temperature for 24 hours. The resulting conjugate was placed in a dialysis tube (10,000 MW cut-off) and was dialyzed in 1 L of 30% DMSO in 50 mM potassium phosphate (pH 7.5, 3 changes, at least 3 hours each), 1 L of 20% DMSO in 50 mM potassium phosphate (at least 3 hours), 1 L of 10% DMSO in 50 mM potassium phosphate (at least 3 hours), followed by 6 changes with 50 mM potassium phosphate (pH 7.5) at 4° C. (1 L each for at least 6 hours each). The protein concentration was determined to be 0.9 mg/mL using BioRad Coomassie blue protein assay (Bradford, M., *Anal. Biochem.* 72:248,1976). A total of 15 mL of the conjugate was obtained.

EXAMPLE 35

MDEA 2IT-KLH (2S)

Keyhole limpet hemocyanin (KLH, 60 mg) was reconstituted in 100 mM sodium phosphate buffer at pH 7.2. 2-Iminothiolane (2IT, 13.5 mg) was added to the protein solution as a solid, and the reaction was allowed to stir at room temperature in the dark and under argon atmosphere for 1 hour. The activated KLH—(SH)$_n$ was desalted on a Sephadex PD-10 column pre-equilibrated with 100 mM sodium phosphate buffer at pH 6.5. The SH loading was determined (Ellman's reagent) to be 886 per KLH molecule (MW 5,000,000). To 6 ml of KLH—(SH)$_n$, 4.7 mg/mL, was added a solution of 14 mg (0.027 mmol) of MDEA-maleimide (2O) in 1 mL of DMF dropwise, and the mixture was allowed to stir at room temperature 18 hours. The resulting conjugate was placed in a dialysis tube (10,000 MW cut-off) and was dialyzed in 1 L of phosphate buffered saline (PBS) buffer (180 mM NaCl, 10 mM sodium phosphate, pH 7.2] containing 20% DMF. (3 times, at least 6 hours each). This was followed by 1 L of PBS buffer, pH 7.2 at 4° C. The protein concentration was determined to be 2.08 mg/mL using Biorad Coomassie blue protein assay (Bradford, M., *Anal. Biochem.* 72:248, 1976). A total of 20 mL of the conjugate was obtained.

EXAMPLE 36

2-(3,4-dimethoxy-phenyl)-1-methyl-ethylamine (3A)

To 2 g (10.29 mmol) of 3,4-dimethoxyphenyl acetone was added 10 mL of methanol, 7.9 g (102 mmol) of ammonium acetate, 844 mg (10.2 mmol) of sodium acetate and 970 mg (15.4 mmol) of sodium cyanoborohydride. The pH of the reaction was adjusted to between 6-7 by addition of glacial acetic acid. The reaction mixture was allowed to stir at room temperature 18 hours and concentrated under reduced pressure. To the residue 100 mL of water was added, and the pH of the reaction was adjusted to 14 using 6 N NaOH. The aqueous layer was extracted with 6×30 mL of chloroform. Organic layers were combined, dried (Na$_2$SO$_4$) and concentrated under reduced pressure to give 2 g (10.24 mmol, 99%) of 3A as a light yellow gum (M+H 196).

EXAMPLE 37

4-(2-amino-propyl)-benzene-1,2-diol Compound with Hydrobromic Acid Salt (3B)

To 2.0 g of 3A (2.01 mmol) was added 48% HBr, and the mixture was heated on a preheated oil bath for 3 hours under argon atmosphere. The reaction mixture was concentrated under reduced pressure to give thick oil. To the residue, 75 mL of dichloromethane was added and concentrated to dryness under reduced pressure. This was repeated four more times to give 2.3 g of 3B as light pink powder (M+H, 168).

EXAMPLE 38

[2-(3,4-dihydroxy-phenyl)-1-methyl-ethyl]-carbamic Acid Tert-Butyl Ester (3C)

To all of 3B from the above reaction mixture was added 50 mL of 50% THF in water. To the reaction mixture 2.4 g of sodium bicarbonate was added as a solid followed by 3.02 g (13.8 mmol) of di-t-butyl dicarbonate in 7 mL of THF dropwise over a period of 30 minutes. The reaction mixture was allowed to stir at room temperature 18 hours and concentrated under reduced pressure. This was diluted with 50 mL of water, and the pH of the solution was adjusted to 5. The aqueous layer was extracted with 3×100 mL of ethyl acetate. The organic layers were combined, dried (Na$_2$SO$_4$) and concentrated. The residue was purified by silica gel column chromatography using 40% ethyl acetate in hexane to give 1.3 g (4.6 mmol, 46%) of 3C as a white sticky foam (M+Na, 290).

EXAMPLE 39

5-(2-tert-butoxycarbonylamino-propyl)-benzo[1,3]dioxole-2-carboxylic Acid Ethyl Ester (3D)

To 1.30 g (4.6 mmol) of 3C was added 40 ml of anhydrous DMF followed by 2.5 g (18 mmol) of anhydrous K$_2$CO$_3$, 2.5 g of 3 A° molecular sieves and 2.3 mL (17.7 mmol) of ethyldibromoacetate. The reaction mixture was heated at 120° C. for 3 hours under argon atmosphere and concentrated under reduced pressure. To the residue 100 mL of water and 75 mL of ethyl acetate were added and filtered. The filtrate was transferred to a separatory funnel and the organic layer was separated. The aqueous layer was extracted with 4×50 mL of ethyl acetate. All the organic layers were combined, dried (Na$_2$SO$_4$) and concentrated. The residue was purified by silica gel column chromatography using 20% ethyl acetate in hexane to give 413 mg (1.17 mmol, 26%) of 3D as a colorless gum (M+Na, 374).

EXAMPLE 40

2(2-carbamoyl-benzo[1,3]dioxol-5-yl)-1-methylethyl]-carbamic Acid Tert-butyl Ester (3E)

To 413 mg (1.17 mmol) of 3D was added 30 mL of anhydrous methanol, and ammonia gas was passed through the solution for 1 hour at room temperature. The mixture was concentrated and purified by silica gel column chromatography using 30% hexane in ethyl acetate to give crude product. This was purified by silica gel column chromatography using 30% ethyl acetate in hexane to give 356 mg (1.10 mmol, 94%) of 3E as a colorless gum (M+Na, 345).

EXAMPLE 41

[2-(2-aminomethyl-benzo[1,3]dioxo-5-yl)-1-methylethyl]-carbamic Acid Tert-butyl Ester (3F)

A flask containing 7 mL of freshly distilled THF was cooled to −60° C., and 76 mg (2.0 mmol) of lithium aluminium hydride was added To the reaction mixture a solution of 214 mg (0.66 mmol) of 3E in 7 mL of freshly distilled THF was added dropwise under argon atmosphere. The reaction mixture was allowed to warm up to room temperature and allowed to stir for 2 hours at room temperature. To the reaction mixture was added 70 μL of 15% NaOH and 570 μL of water and allowed to stir at room temperature for 10 minutes. The resulting solution was filtered through CELITE and the residue was washed with 50 mL of THF. The filtrate was concentrated under reduced pressure and purified by silica gel column chromatography using first ethyl acetate and then 10% methanol in ethyl acetate as eluent to give 46 mg (0.15 mmol, 23%) of 3F as a colorless gum (M+Na, 331).

EXAMPLE 42

N-[5-(2-tert-butoxycarbonylamino-propyl)-benzo[1,3]dioxol-2-ylmethyl]-succinamic Acid (3G)

To a solution of 46 mg (0.15 mmol) of 3F in 4 mL of 1,2 dichloroethane was added 46 mg (0.46 mmol) of succinic anhydride and 22 mg (0.18 mmol) of 4-DMAP. The reaction mixture was allowed to stir at 40° C. under argon atmosphere

23 for 2.5 hours. This was diluted with 50 mL of ethyl acetate and washed with 3×30 mL of 5% ammonium chloride solution. The organic layer was dried ($Na_2SO_4$) and concentrated under reduced pressure. The residue was purified by silica gel column chromatography using ethyl acetate as eluent to give 36 mg (0.08 mmol, 60%) of 3G as a colorless gum (M+Na, 431).

EXAMPLE 43

N-[5-(2-tert-butoxycarbonylamino-propyl)-benzo[1,3]dioxol-2-ylmethyl]-succinamic Acid 2,5-dioxo-pyrrolidin-1-yl Ester (3H)

To 32 mg (0.078 mmol) of 3G was added 4 mL of dichloromethane (distilled over $CaH_2$) followed by 14 mg (0.12 mmol) of N-hydroxysuccinimide and 30 mg (0.152 mmol) of 1-ethyl-3-(3-dimethylaminopropyl)-carbodiimide. The reaction mixture was allowed to stir at room temperature under argon atmosphere 18 hours. The reaction mixture was diluted with additional 25 mL of dichloromethane and washed with 2×20 mL of water, 2×20 mL of saturated sodium bicarbonate and 1×20 mL of water. The organic layer was dried ($Na_2SO_4$) and concentrated to give 36 mg (0.071 mmol) of 3H as a colorless gum.

EXAMPLE 44

MDA-Aminodextran Conjugate (3I)

To a 3 L three-necked flask equipped with a mechanical stirrer was added 700 mL of deionized water. Dextran (70 g, 1.86 mmol) having a molecular weight of 37,500 (Sigma-Chemicals, Milwaukee, Wis.) was added gradually to the flask while stirring the mixture, dissolving the dextran in the water at room temperature. To the reaction mixture, 140 mL of 1N NaOH was added, and the reaction was heated to 30-35° C. A solution of 79 mL (923 mmol) of epibromohydrin in 245 mL of 1,4-dioxane was then added dropwise at 30-35° C. over a period of 45 minutes. The resulting mixture was stirred and heated at 30-35° C. for an additional 4 hours. The reaction mixture was allowed to cool to room temperature and was then transferred to a 2 L separatory funnel. The organic layer slowly separated as the bottom layer was discarded. The aqueous mixture was transferred into a 3 L flask and cooled in an ice-bath. A solution of 700 mL of 25% ammonium hydroxide was then added to the reaction flask, and the pH was adjusted to pH 11 with 1N HCl. The resulting solution was allowed to warm up to room temperature overnight. The reaction mixture was transferred to a dialysis tubing (MW cut-off 2000) and dialyzed in two 12 L containers according to the following schedule, using a 20 L solvent for each step: 1% acetic acid for 6 hours, 1% acetic acid for 24 hours, 1% acetic acid for 48 hours, and deionized water for 24 hours (6 times).

The solution was concentrated by rotary evaporation to one third volume and then lyophilized to give 48 g of product as a white solid. By using TNBS assays, the product was found to contain 5.7 amino groups for every mole of aminodextran (Anal. Biochem. 64, 284-288, 1975). This aminodextran was used to prepare MDA-aminodextran conjugate.

To 78 mg of aminodextran was added 5 mL of DMSO at room temperature. The mixture was allowed to stir at room temperature for 10 minutes until all aminodextran went into solution. The MDA derivative 3H (9.6 mg, 0.2 mmol) was dissolved in 1 mL of anhydrous DMSO and added dropwise to the stirred aminodextran solution. The mixture was allowed to stir at room temperature for 18 hours and was transferred into Spectrapor dialysis tubing (MW cut-off 2000) and dialyzed (each dialysis using 1 L volume) according to the following schedule: 60% DMSO in 40% deionized water at room temperature (3 times, at least 3 hours each); 50% DMSO in 50% deionized water at room temperature (2 times, for at least 3 hours each); 30% DMSO in 70% deionized water (1 time, for at least 3 hours); 10% DMSO in 90% deionized water (1 time, for at least 3 hours); and deionized water at room temperature (6 times, for at least 6 hours each).

The solution was taken out of the dialysis tubing and lyophilized to give 64 mg of protected MDA-aminodextran conjugate as a white powder. This protected conjugate was ready for the deprotection step.

To all of the above protected MDA-dextran conjugate was added 2 mL of dichloromethane, and the suspension was allowed to stir at room temperature for 30 minutes. To the reaction mixture 2 mL of trifluoroacetic acid was slowly added, and this was allowed to stir at room temperature for 10 minutes. The reaction mixture was concentrated to dryness under reduced pressure, and the residue was dissolved in 10 mL of deionized water. The reaction mixture was transferred into a dialysis tubing (MW cut-off 2000) and dialyzed against 1 L of deionized water (4 times, at least 6 hours each). The solution was taken out of the dialysis tubing and lyophilized to give 53 mg of MDA-aminodextran conjugate (3I) as a white powder.

EXAMPLE 45

Production of MDMA 8.3 Clone and Antibody

Immunizations

Female Balb/C mice 16 weeks of age or older were immunized by multiple injections of the immunogens as follows. 100 μg of MDMA immunogen 1P per mouse was mixed with an equal volume of RIBI immunogen (Sigma Chemicals) for 2-3 minutes and loaded into an appropriately sized syringe fitted with a 37 gauge hypodermic needle. Each mouse received a 100 μg dose of immunogen with adjuvant via intraperitoneal injection. Thirty nine days later, the same mice received another injection identical to the first. The injections were repeated on day 60 and again on day 80. On day 192, one mouse was given a 150 μg injection prepared as described above and via the same route. This animal was used for fusion four days later.

Fusion and Development of Monoclonal Antibodies

The mouse chosen for fusion was exsanguinated via retro-orbital bleeding to collect serum and subsequently cervically dislocated. The spleen was removed using aseptic technique and placed in 10 mL of complete culture medium (Iscove's Modified Dulbecco's medium (IMDM), Irvine Scientific) in a sterile petri dish. The spleen was then ground between two sterile frosted microscope slides. The resulting cell suspension was allowed to stand in a 15 mL centrifuge tube for 1-2 minutes to allow large particulates to settle. The resulting single-cell suspension was drawn off and counted using a hemocytometer. FO myeloma cells (CRL-1646, American Type Culture Collection) were mixed into the spleen cells in a ratio of 1:5, FO myeloma cells:spleen cells and centrifuged for 15 minutes at about 800×G. The supernatant liquid was drawn off and discarded, and 15 mL of serum-free IMDM culture media was added. The cells were re-suspended and again centrifuged. The resulting cell pellet was fused using polyethylene glycol/DMSO according to the method of Fazekas de St. Groth, *J. Immunol. Meth.* 35:1-21, 1980.

After fusion, the cells were diluted to 2×10⁵ splenic lymphocytes per mL in complete Iscove's Modified Dulbecco's medium (high glucose) supplemented with 10% fetal bovine serum (Hyclone Labs), 10% Condimed HI (Roche Molecular Chemicals), 50 mM 2-mercaptoethanol, 20 mM ethanolamine, hypoxanthine-methotrexate-thymidine (HMT, Sigma Chemicals, diluted 1:50 for use), 4 mM glutamine and Pen/Strep antibiotics (Irvine Scientific). This mixture of fused cells was plated at 200 µL/well into sterile 96-well microculture plates. The covered plates were placed in an incubator for 6 days at 37° C. in 5% $CO_2$. On the sixth day, approximately 150 µL of medium was removed via an eight place vacuum manifold, and 150 µL of HT-IMDM was added. This media was prepared as described above, with the exception that hypoxanthine-thymidine (HT, Sigma, diluted 1:50) was substituted for the HMT. The plates were incubated as previously described until visual inspection revealed growth suitable for screening, about 50% confluency.

Screening

The screening consisted of an enzyme-linked immunosorbant assay (ELISA) in which 0.1 mL MDMA-BSA (1O) was adsorbed to the plastic wells at a concentration of 1 mg/mL for one hour at 37° C. The wells were then rinsed with PBS-TWEEN (phosphate buffered saline with 0.05% TWEEN 20) and blocked with 200 µL of Post Coat solution (1% gelatin hydrolysate, 2% sucrose in 0.15 M Tris, pH 7.2-7.4) for one hour at room temperature. The plates were then rinsed with 2% sucrose, air dried, and stored in desiccated sealed plastic bags at 4° C. until used.

To perform the screening assay, two plates coated with MDMA-BSA were prepared by pipetting into separate wells 25 µL of PBS-TWEEN and 25 µL of a 400 ng/mL solution of free MDMA in PBS-TWEEN. Cell culture supernatant (25 µL) taken from wells showing at least 50% confluency of cell growth was diluted 1:20 in PBS-TWEEN in flexible microtiter plates (Falcon Plastics). 25 µL of the dilute supernatant was added to a well in each of the four microtiter plates and allowed to incubate covered at 37° C. for one hour. The plates were then washed using a Biotek Elx 300 plate washer and PBS-TWEEN. Goat anti-mouse IgG-HRP (horseradish peroxidase) conjugate (Zymed Labs) was diluted 1:5,000 into PBS-TWEEN just prior to use, and 100 mL was added to all wells of all four plates. The plates were again incubated covered at 37° C. for one hour. The plates were washed as above, and 100 mL of K Blue Substrate (Neogen) was added. The color was allowed to develop for 5 minutes at room temperature in the dark. The development was halted by the addition of 100 µL of 1 N HCl, and color was read at 450 nm using a microplate reader (Molecular Devices Corp.). Data was captured on a Macintosh computer and tabulated to show the $OD_{450}$ of each well of the different plates per culture well tested.

Cell lines showing production of antibody which provided a good binding to MDMA-BSA (high OD) and good competition by free MDMA (low OD) were selected for further work. Selected hybridomas were immediately subjected to stringent subcloning by limiting dilution in the culture media described above. Upon growth to about 50% confluency, the hybridomas were re-tested by a method similar to the one described above in which binding to MDMA-BSA and competition by free MDMA or MDEA is examined. Clones showing good binding to MDMA-BSA and competition by either free drug were selected for specificity analysis and cell banking. If all subclones of a particular cell line did not perform approximately equally, this was taken as evidence of instability, and three wells were used for another cycle of subcloning. This procedure was repeated until each line of hybridoma was stable. Upon stability, the cells were expanded in culture, and samples were frozen at –80° C. in vapor-phase liquid nitrogen for storage. Samples of the culture supernatant were saved for specificity analysis.

Specificity Determination

The binding specificity of the monoclonal antibody was determined using a drug competitive ELISA assay. Plates coated with MDMA-BSA at 0.1 µg/mL (other conditions as described above) were used. Antibody titer was determined from the hybridoma culture supernatants described above through assay of serial dilutions of the supernatants incubated on the coated plates. The $OD_{450}$ for each supernatant at each dilution was plotted versus the dilution factor. From that data, the dilution factor providing for 50-60% of the maximal $OD_{450}$ was determined. This dilution was then used for the competitive inhibition assay using the same type of plates as for the titer determination.

To prepare the competitor drugs, the following free drugs were dissolved in methanol to 1 mg/mL: MDMA, MDEA, MDA, MBDB, BDB, d-amphetamine, d-methamphetamine, l-amphetamine, and l-methamphetamine. These stock solutions were diluted in PBS-TWEEN at a ratio of 1:333, and 100 µL of each was transferred to row A of a microtiter plate. These solutions were serially diluted by transferring 50 µL from row A into wells of row B containing 100 µL of PBS-TWEEN and mixed by pipette. This dilution process was repeated until seven rows of the microtiter plate contained serial dilutions of the free drug solutions. The eighth row was left with zero drug.

Plates coated with MDMA-BSA at 0.1 µg/mL were prepared as described above. A 25 µL aliquot of each dilution of each free drug was transferred to a fresh conjugate-coated plate. To these solutions was added 25 µL of diluted hybridoma culture supernatant. By this procedure, 9 cross-reactants, i.e., the cross-reactants described above including the drug standard MDMA, were screened on a single antibody per plate. The competition assays were incubated at 37° C. for one hour. The plates were then washed using a Biotek Elx 300 plate washer and PBS-TWEEN. Goat anti-mouse IgG-horseradish peroxidase (IgG-HRP) conjugate (Zymed Labs) was diluted 1:5,000 into PBS-TWEEN just prior to use, and 100 µL was added to all wells of all four plates. The plates were again incubated covered at 37° C. for one hour. The plates were washed as above, and 100 µL of K Blue substrate (Neogen) was added. The color was allowed to develop for 5 minutes at room temperature in the dark. The development was halted by the addition of 100 µL of 1 N HCl, and color was read at 450 nm using a Molecular Devices Corp. microplate reader. Data was captured on a Macintosh computer. $OD_{450}$ values were graphed for each of the various concentrations of free drug competitor ($10^{-12}$-$10^{-4}$ M).

Data from this specificity determination method was used to calculate the percent cross-reactivity of each antibody to the different drugs as compared to the immunizing drug, MDMA. This was accomplished by analyzing the data to determine the $ED_{50}$ for each drug. The $ED_{50}$ is the measure of the effective concentration of free competitor drug (MDEA, MDA, etc.) required to inhibit monoclonal antibody binding to conjugate-bound MDMA by 50%. The cross-reaction was calculated by dividing the $ED_{50}$ of the standard by the $ED_{50}$ of the drug being considered, and percent cross-reaction was calculated by multiplying the cross-reactivity by 100. This analysis showed that one clone, designated MDMA 8.3, unexpectedly showed an 89-fold higher affinity for the drug MDEA than for the immunizing drug MDMA. This clone also unexpectedly showed a 4.6-fold higher affinity for MDA than for MDMA. These findings are summarized in Table 1 below.

TABLE 1

Specificity determination of MDMA 8.3, % cross-reaction

| Clone | MDMA | MDEA | MDA | MBDB | BDB | d-AMP | d-MAMP | l-AMP | l-MAMP |
|---|---|---|---|---|---|---|---|---|---|
| 8.3 | 100 | 8,879 | 464 | 0 | 0 | 0 | 0 | 0 | 0 |

The murine hybridoma cell line MDMA 8.3 was deposited with the American Type Culture Collection (ATCC, Manassas, Va.) on Jul. 23, 2003 and assigned ATCC designation PTA-5340.

EXAMPLE 46

Production of MDMA 6.1 Hybridoma and Monoclonal Antibody

Immunizations

Female Balb/C mice 16 weeks of age or older were immunized by multiple injections of the immunogens according to the following schedule. 100 µg of MDMA immunogen 1P per mouse was mixed with an equal volume of RIBI immunogen (Sigma Chemicals) for 2-3 minutes and loaded into an appropriately sized syringe fitted with a 37 gauge hypodermic needle. Each mouse received a 100 µg dose of immunogen with adjuvant via intraperitoneal injection. Thirty-nine days later, the same mice received another injection identical to the first. The injections were repeated on day 60 and again on day 80. One animal was used for fusion four days later.

Fusion and Development of Monoclonal Antibodies

All methods of animal handling, cell culture and fusion were as described above in Example 45.

Screening

The same methods were employed as described in Example 45.

Specificity

Specificity determinations were made as described in Example 45. An antibody developed in this example, in contrast to previous findings, was unexpectedly found to show a high degree of cross-reaction for d-methamphetamine. This clone, designated MDMA 6.1, showed essentially the same affinity for d-methamphetamine and for MBDB as for MDMA, as shown in the table below.

TABLE 2

Specificity determination of MDMA 6.1, % cross-reaction

| Clone | MDMA | MDEA | MDA | MBDB | BDB | d-AMP | d-MAMP | l-AMP | l-MAMP |
|---|---|---|---|---|---|---|---|---|---|
| 6.1 | 100 | 43.1 | 0.3 | 100 | 3.4 | 0.007 | 95.5 | 0 | 2.1 |

The murine hybridoma cell line MDMA 6.1 was deposited with the American Type Culture Collection (ATCC, Manassas, Va.) on Jul. 23, 2003 and assigned ATCC designation PTA-5339.

EXAMPLE 47

Production of Clone and Monoclonal Antibody MDEA 2.2

Immunizations

Female Balb/C mice 16 weeks of age or older were immunized by multiple injections of the immunogens according to the following schedule. 100 µg of MDEA immunogen 2U per mouse was mixed with an equal volume of RIBI immunogen (Sigma Chemicals) for 2-3 minutes and loaded into an appropriately sized syringe fitted with a 37 gauge hypodermic needle. Each mouse received a 100 µg dose of immunogen with adjuvant via intraperitoneal injection. Thirty-nine days later, the same mice received another injection identical to the first. The injections were repeated on day 60 and again on day 80. The injections were repeated on day 137, and 4 days later, one mouse was used for fusion.

Fusion and Development of Monoclonal Antibodies

All methods of animal handling, cell culture, and fusion were as described in Example 45.

Screening

The same methods were employed as in Example 45 with several substitutitons. MDEA-BSA (2T) was employed as the plate coating, replacing the MDMA-BSA (1O) in Example 45. Competitive binding also used MDEA in addition to the MDMA in Example 45.

Specificity

Specificity determinations were as set forth in Example 45, with MDEA-BSA (2T) being substituted for the MDMA-BSA (1O). The percent cross-reactions determined for two antibodies from this fusion are presented in Table 3 below. Antibody MDEA 1.1 is an example of the expected cross-reactivity profile given the immunogen used to raise the immune response in the mice.

TABLE 3

MDEA monoclonal antibody specificities

| Clone | MDEA | MDMA | MDA | MBDB | BDB | d-AMP | d-MAMP | l-AMP | l-MAMP |
|---|---|---|---|---|---|---|---|---|---|
| 1.1 | 100 | 26 | 0 | 3.04 | 0 | 0 | 0.6 | 0 | 3.5 |
| 2.2 | 100 | 412 | .1 | 4,360 | 2.3 | 0 | 30.7 | 0 | 2.5 |

The murine hybridoma cell line MDEA 2.2 was deposited with the American Type Culture Collection (ATCC, Manassas, Va.) on Jul. 23, 2003, 2003 and assigned ATCC designation PTA-5338.

The stimulating immunogen used to raise the immune response in the mouse used for fusion was MDEA-KLH, therefore it is to be expected that the highest affinity observed in the resulting monoclonal antibodies would be to that moiety. This is what was seen for clone MDEA 1.1, with cross-reactions to the other drugs being relatively minor. Clone MDEA 2.2 showed several unexpected departures from that behavior. The affinity for MDMA was 412% of that for MDEA, and for MBDB, it was a very unexpected 4,360% higher.

What is claimed is:

1. Cell line MDMA 8.3, ATCC designation PTA-5340, producing a monoclonal antibody having greater than 100% cross-reactivity to MDEA (3,4-methylenedioxyethylamphetamine) based on the monoclonal antibody having a 100% cross-reactivity to MDMA (3,4-methylenedioxymethamphetamine).

2. A monoclonal antibody produced from cell line MDMA 8.3, ATCC designation PTA-5340, the antibody having greater than 100% cross-reactivity to MDEA (3,4-methylenedioxyethylamphetamine) based on the monoclonal antibody having a 100% cross-reactivity to MDMA (3,4-methylenedioxymethamphetamine).

3. Cell line MDMA 6.1, ATCC designation PTA-5339, producing a monoclonal antibody specific for an analyte comprising a conjugate of MDMA. (3,4-methylenedioxymethamphetamine) and an immunogenic: carrier wherein the immunogenic carrier is linked to the MDMA at the carbon position of the methylenedioxy moiety and having greater than 90% cross-reactivity to MBDB (3,4-methylenedioxy-N-methylbutanamine) and d-MAMP (d-methamphetamine) based on the monoclonal antibody having a 100% cross-reactivity to MDMA.

4. A monoclonal antibody produced from cell line MDMA 6.1, ATCC designation PTA-5339 and specific for an analyte comprising a conjugate of MDMA (3,4-methylenedioxymethamphetamine) and an immunogenic carrier wherein the immunogenic carrier is linked to the MDMA at the carbon position of the methylenedioxy moiety, the antibody having greater than 90% cross-reactivity to MBDB (3,4-methylenedioxy-N-methylbutanamine) and d-MAMP (d-methamphetamine) based on the monoclonal antibody haying a 100% cross-reactivity to MDMA.

5. Cell line MDEA 2.2, ATCC designation PTA-5338, producing a monoclonal antibody specific for an analyte comprising a conjugate of MDEA (3,4-methylenedioxyethylamphetamine) and an immunogenic carrier wherein the immunogenic carrier is linked to the MDEA at the carbon position of the methylenedioxy moiety and having greater than 100% cross-reactivity to MDMA (3,4-methylenedioxymethamphetamine) and MBDB (3,4-methylenedioxy-N-methylbutanamine) based on the monoclonal antibody having a 100% cross-reactivity to MDEA.

6. A monoclonal antibody produced from cell line MDEA 2.2, ATCC designation PTA-5338 and specific for an analyte comprising a conjugate of MDEA (3,4-methylenedioxyethylamphetamine) and an immunogenic carrier wherein the immunogenic carrier is linked to the MDEA at the carbon position of the methylenedioxy moiety, the antibody having greater than 100% cross-reactivity to MDMA (3,4-methylenedioxymethamphetamine) and MBDB (3,4-methylenedioxy-N-methylbutanamine) based on the monoclonal antibody having a 100% cross-reactivity to MDEA.

* * * * *